(12) United States Patent
Jo et al.

(10) Patent No.: US 11,417,844 B2
(45) Date of Patent: Aug. 16, 2022

(54) COMPOSITION FOR ORGANIC OPTOELECTRONIC DEVICE, ORGANIC OPTOELECTRONIC DEVICE, AND DISPLAY DEVICE

(71) Applicant: SAMSUNG SDI CO., LTD., Yongin-si (KR)

(72) Inventors: Youngkyoung Jo, Suwon-si (KR); Jinhyun Lui, Suwon-si (KR); Yongtak Yang, Suwon-si (KR); Jaejin Oh, Suwon-si (KR); Eun Sun Yu, Suwon-si (KR); Hanill Lee, Suwon-si (KR); Sung-Hyun Jung, Suwon-si (KR); Ho Kuk Jung, Suwon-si (KR); Pyeongseok Cho, Suwon-si (KR); Dalho Huh, Suwon-si (KR)

(73) Assignee: SAMSUNG SDI CO., LTD., Yongin-si (KR)

( * ) Notice: Subject to any disclaimer, the term of this patent is extended or adjusted under 35 U.S.C. 154(b) by 454 days.

(21) Appl. No.: 16/478,564

(22) PCT Filed: Oct. 26, 2017

(86) PCT No.: PCT/KR2017/011926
§ 371 (c)(1),
(2) Date: Jul. 17, 2019

(87) PCT Pub. No.: WO2018/159916
PCT Pub. Date: Sep. 7, 2018

(65) Prior Publication Data
US 2019/0348612 A1    Nov. 14, 2019

(30) Foreign Application Priority Data

Feb. 28, 2017  (KR) .......................... 10-2017-0026359
Oct. 26, 2017  (KR) .......................... 10-2017-0140114

(51) Int. Cl.
*H01L 51/00*    (2006.01)
*C09K 11/02*    (2006.01)
(Continued)

(52) U.S. Cl.
CPC ........ *H01L 51/0067* (2013.01); *C07D 251/24* (2013.01); *C07D 405/10* (2013.01);
(Continued)

(58) Field of Classification Search
None
See application file for complete search history.

(56) References Cited

U.S. PATENT DOCUMENTS 5,942,340 A     8/1999  Hu et al.
2014/0231769 A1* 8/2014  Nishimura .......... H01L 51/0055
                                         257/40

(Continued)

FOREIGN PATENT DOCUMENTS

KR   10-2014-0015298 A    2/2014
KR   10-2015-0007476 A    1/2015
(Continued)

OTHER PUBLICATIONS

International Search Report for PCT/KR2017/011926 filed on Oct. 26, 2017.

*Primary Examiner* — Robert S Loewe
(74) *Attorney, Agent, or Firm* — Lee IP Law, P.C.

(57) ABSTRACT

The present invention relates to a composition for an organic optoelectronic device, an organic optoelectronic device employing the composition, and a display device, wherein the composition includes: at least one first compound for an organic optoelectronic device, represented by chemical formula 1; and a second compound for an organic optoelectronic device, represented by a combination of Chemical Formula 2 and Chemical Formula 3A or a combination of
(Continued)

Chemical Formula 2 and Chemical Formula 3B. The details of Chemical Formulae 1, 2, 3A, and 3B are as defined in the specification.

11 Claims, 1 Drawing Sheet

(51) Int. Cl.
    *C07D 487/04*     (2006.01)
    *C07D 251/24*     (2006.01)
    *C07D 405/10*     (2006.01)
    *H01L 51/50*     (2006.01)

(52) U.S. Cl.
    CPC .......... *C07D 487/04* (2013.01); *C09K 11/025* (2013.01); *H01L 51/0072* (2013.01); *H01L 51/0073* (2013.01); *H01L 51/5012* (2013.01); *H01L 51/5056* (2013.01); *H01L 51/5072* (2013.01); *H01L 51/5088* (2013.01); *H01L 51/5092* (2013.01); *H01L 51/5096* (2013.01)

(56) References Cited

U.S. PATENT DOCUMENTS

| | | | |
|---|---|---|---|
| 2015/0102301 A1* | 4/2015 | Cho | H01L 51/0054 257/40 |
| 2015/0349268 A1* | 12/2015 | Zeng | H01L 51/0067 257/40 |
| 2016/0126472 A1* | 5/2016 | Oh | C07D 405/04 257/40 |
| 2016/0133844 A1* | 5/2016 | Kim | H01L 51/0054 257/40 |
| 2016/0293853 A1* | 10/2016 | Zeng | H01L 51/0067 |
| 2016/0293854 A1* | 10/2016 | Zeng | C09K 11/025 |
| 2016/0293855 A1* | 10/2016 | Zeng | H01L 51/0074 |
| 2017/0025618 A1 | 1/2017 | Zheng et al. | |
| 2017/0069848 A1* | 3/2017 | Zeng | H01L 51/0072 |
| 2017/0104163 A1* | 4/2017 | Lee | C09K 11/06 |
| 2017/0170405 A1* | 6/2017 | Cho | H01L 51/0073 |
| 2017/0267923 A1* | 9/2017 | Li | H01L 51/5012 |
| 2017/0271598 A1* | 9/2017 | Zeng | H05B 33/20 |
| 2017/0309831 A1* | 10/2017 | Kim | C07D 251/24 |
| 2018/0145268 A1* | 5/2018 | Ma | H01L 51/5072 |
| 2019/0157569 A1* | 5/2019 | Lee | C07D 487/04 |

FOREIGN PATENT DOCUMENTS

| | | |
|---|---|---|
| KR | 10-2015-0030511 A | 3/2015 |
| KR | 10-2015-0042650 A | 4/2015 |
| KR | 10-2015-0137400 A | 12/2015 |
| KR | 10-2016-0006633 A | 1/2016 |
| KR | 10-2016-0007966 A | 1/2016 |
| KR | 10-2016-0046078 A | 4/2016 |
| KR | 10-1618683 B1 | 4/2016 |
| KR | 10-2016-0050700 A | 5/2016 |
| KR | 10-2016-0055556 A | 5/2016 |
| KR | 10-1649683 B1 | 8/2016 |
| KR | 10-2016-0119712 A | 10/2016 |
| KR | 10-2017-0086277 A | 7/2017 |
| KR | 10-2018-0013449 A | 2/2018 |
| WO | WO 2016-017514 A1 | 2/2016 |

* cited by examiner

[Figure 1]
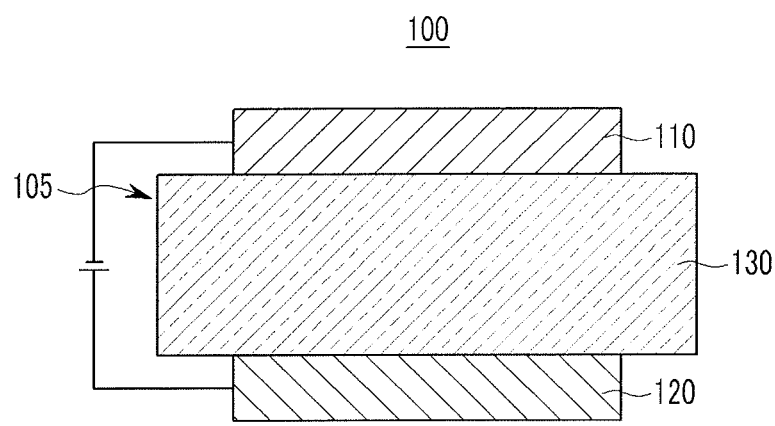
[Figure 2]
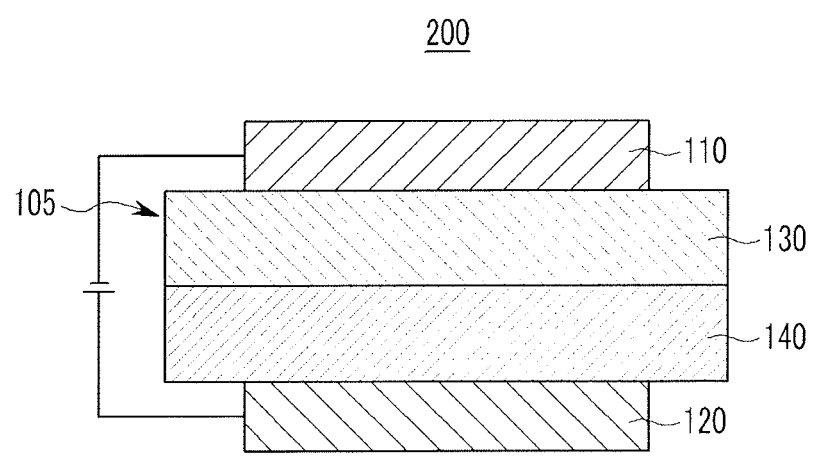

COMPOSITION FOR ORGANIC OPTOELECTRONIC DEVICE, ORGANIC OPTOELECTRONIC DEVICE, AND DISPLAY DEVICE

CROSS-REFERENCE TO THE RELATED APPLICATION

This is the U.S. national phase application based on PCT Application No. PCT/KR2017/011926, filed Oct. 26, 2017, which is based on Korean Patent Application No. 10-2017-0026359, filed Feb. 28, 2017, and Korean Patent Application No. 10-2017-0140114, filed Oct. 26, 2017, the entire contents of all of which are hereby incorporated by reference.

TECHNICAL FIELD

A composition for an organic optoelectronic device, an organic optoelectronic device, and a display device are disclosed.

BACKGROUND ART

An organic optoelectronic device is an element that converts electrical energy into photoenergy, and vice versa.

An organic optoelectronic device may be classified as follows in accordance with its driving principles. One is a photoelectric element where excitons are generated by photoenergy, separated into electrons and holes, and are transferred to different electrodes to generate electrical energy, and the other is a light emitting element where a voltage or a current is supplied to an electrode to generate photoenergy from electrical energy.

Examples of the organic optoelectronic device may be an organic photoelectric element, an organic light emitting diode, an organic solar cell, and an organic photo conductor drum.

Of these, an organic light emitting diode (OLED) has recently drawn attention due to an increase in demand for flat panel displays. The organic light emitting diode is an element converting electrical energy into light by applying a current to an organic light emitting material, and has a structure in which an organic layer is disposed between an anode and a cathode. Herein, the organic layer may include a light emitting layer and optionally an auxiliary layer, and the auxiliary layer may be for example at least one layer selected from a hole injection layer, a hole transport layer, an electron blocking layer, an electron transport layer, an electron injection layer, and a hole blocking layer.

Performance of an organic light emitting diode may be affected by characteristics of the organic layer, and among them, may be mainly affected by characteristics of an organic material of the organic layer.

Particularly, development for an organic material capable of increasing hole and electron mobility and simultaneously increasing electrochemical stability is needed so that the organic light emitting diode may be applied to a large-size flat panel display.

DISCLOSURE

An embodiment provides a composition for an organic optoelectronic device capable of realizing high efficiency and long life—organic optoelectronic device.

Another embodiment provides an organic optoelectronic device including the composition.

Yet another embodiment provides a display device including the organic optoelectronic device.

According to an embodiment, a composition for an organic optoelectronic device includes at least one first compound for an organic optoelectronic device represented by Chemical Formula 1; and a second compound for an organic optoelectronic device, represented by a combination of Chemical Formula 2 and Chemical Formula 3A or a combination of Chemical Formula 2 and Chemical Formula 3B.

[Chemical Formula 1]

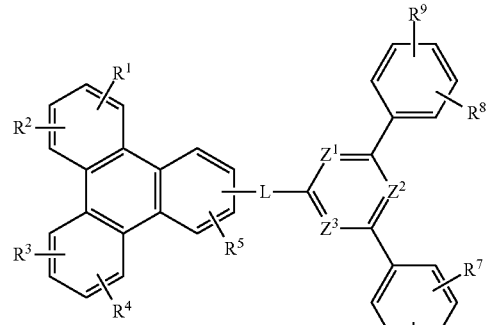

[Chemical Formula 2]

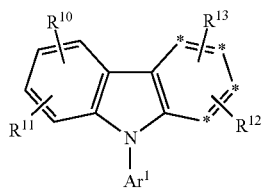

[Chemical Formula 3A]

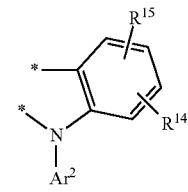

[Chemical Formula 3B]

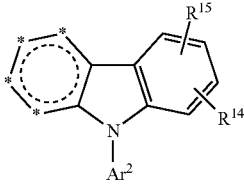

In Chemical Formula 1, $Z^1$ to $Z^3$ are each independently N or $CR^a$, at least two of $Z^1$ to $Z^3$ are N, L is a single bond, or a substituted or unsubstituted C6 to C18 arylene group, $R^a$ and $R^1$ to $R^9$ are each independently hydrogen, deuterium, a hydroxyl group, a thiol group, a cyano group, a substituted or unsubstituted C1 to C20 alkyl group, or a substituted or unsubstituted C6 to C18 aryl group, and $R^6$ to $R^9$ are each independently present or adjacent groups thereof are linked with each other to form a substituted or unsubstituted dibenzofuranyl group, or a substituted or unsubstituted dibenzothiophenyl group;

wherein, in Chemical Formula 2, Chemical Formula 3A, and Chemical Formula 3B,

Ar¹ and Ar² are each independently a substituted or unsubstituted C6 to C30 aryl group, at least one of Ar¹ and Ar² is a substituted or unsubstituted C12 to C30 aryl group, adjacent two "*" of Chemical Formula 2 are linked with "*" of Chemical Formula 3A or adjacent two "*" of Chemical Formula 3B and remaining "*" of Chemical Formula 2 not linked with Chemical Formula 3A and Chemical Formula 3B and remaining "*" of Chemical Formula 3B not linked with Chemical Formula 2 are C or $CR^b$, $R^b$ and $R^{10}$ to $R^{15}$ are each independently hydrogen; deuterium, a substituted or unsubstituted C1 to C20 alkyl group, or a substituted or unsubstituted C6 to C18 aryl group, and $R^b$ and $R^{10}$ to $R^{15}$ are each independently present or adjacent groups thereof are linked with each other to form a substituted or unsubstituted aliphatic monocyclic ring, aliphatic polycyclic ring, aromatic monocyclic ring, aromatic polycyclic ring, heteroaromatic monocyclic ring or heteroaromatic polycyclic ring.

According to another embodiment, an organic optoelectronic device includes an anode and a cathode facing each other and at least one organic layer disposed between the anode and the cathode, wherein the organic layer includes the composition for an organic optoelectronic device.

According to another embodiment, a display device including the organic optoelectronic device is provided.

An organic optoelectronic device having high efficiency and a long life-span may be realized.

DESCRIPTION OF THE DRAWINGS

FIGS. 1 and 2 are cross-sectional views showing organic light emitting diodes according to embodiments.

MODE FOR INVENTION

Hereinafter, embodiments of the present invention are described in detail. However, these embodiments are exemplary, the present invention is not limited thereto and the present invention is defined by the scope of claims.

In the present specification, when a definition is not otherwise provided, "substituted" refers to replacement of at least one hydrogen of a substituent or a compound by deuterium, a halogen, a hydroxyl group, an amino group, a substituted or unsubstituted C1 to C30 amine group, a nitro group, a substituted or unsubstituted C1 to C40 silyl group, a C1 to C30 alkyl group, a C1 to C10 alkylsilyl group, a C6 to C30 arylsilyl group, a C3 to C30 cycloalkyl group, a C3 to C30 heterocycloalkyl group, a C6 to C30 aryl group, a C2 to C30 heteroaryl group, a C1 to C20 alkoxy group, a C1 to C10 trifluoroalkyl group, a cyano group, or a combination thereof.

In one example of the present invention, "substituted" refers to replacement of at least one hydrogen of a substituent or a compound by deuterium, a C1 to C30 alkyl group, a C1 to C10 alkylsilyl group, a C6 to C30 arylsilyl group, a C3 to C30 cycloalkyl group, a C3 to C30 heterocycloalkyl group, a C6 to C30 aryl group, or a C2 to C30 heteroaryl group. In addition, in specific examples of the present invention, "substituted" refers to replacement of at least one hydrogen of a substituent or a compound by deuterium, a C1 to C20 alkyl group, a C6 to C30 aryl group, or a C2 to C30 heteroaryl group. In addition, in specific examples of the present invention, "substituted" refers to replacement of at least one hydrogen of a substituent or a compound by deuterium, a C1 to C5 alkyl group, a C6 to C18 aryl group, a pyridinyl group, a pyrimidinyl group, a quinolinyl group, an isoquinolinyl group, a quinazolinyl group, a dibenzofuranyl group, or a dibenzothiophenyl group. In addition, in specific examples of the present invention, "substituted" refers to replacement of at least one hydrogen of a substituent or a compound by deuterium, a C1 to C5 alkyl group, a C6 to C18 aryl group, a pyridinyl group, pyrimidinyl group, a dibenzofuranyl group, or a dibenzothiophenyl group. In addition, in specific examples of the present invention, "substituted" refers to replacement of at least one hydrogen of a substituent or a compound by deuterium, a methyl group, an ethyl group, a propanyl group, a butyl group, a phenyl group, a biphenyl group, a terphenyl group, a naphthyl group, a triphenyl group, a fluorenyl group, a pyridinyl group, a pyrimidinyl group, a dibenzofuranyl group, or a dibenzothiophenyl group.

In the present specification, when a definition is not otherwise provided, "hetero" refers to one including one to three heteroatoms selected from N, O, S, P, and Si, and remaining carbons in one functional group.

In the present specification, when a definition is not otherwise provided, "alkyl group" refers to an aliphatic hydrocarbon group. The alkyl group may be "saturated alkyl group" without any double bond or triple bond.

The alkyl group may be a C1 to C30 alkyl group. More specifically, the alkyl group may be a C1 to C20 alkyl group or a C1 to C10 alkyl group. For example, a C1 to C4 alkyl group may have one to four carbon atoms in the alkyl chain, and may be selected from methyl, ethyl, propyl, iso-propyl, n-butyl, iso-butyl, sec-butyl, and t-butyl.

Specific examples of the alkyl group may be a methyl group, an ethyl group, a propyl group, an isopropyl group, a butyl group, an isobutyl group, a t-butyl group, a pentyl group, a hexyl group, a cyclopropyl group, a cyclobutyl group, a cyclopentyl group, a cyclohexyl group, and the like.

In the present specification, "aryl group" refers to a group including at least one hydrocarbon aromatic moiety, and may include a group in which all elements of the hydrocarbon aromatic moiety have p-orbitals which form conjugation, for example a phenyl group, a naphthyl group, and the like, a group in which two or more hydrocarbon aromatic moieties may be linked by a sigma bond, for example a biphenyl group, a terphenyl group, a quarterphenyl group, and the like, and a group in which two or more hydrocarbon aromatic moieties are fused directly or indirectly to provide a non-aromatic fused ring. For example, it may be a fluorenyl group.

The aryl group may include a monocyclic, polycyclic or fused ring polycyclic (i.e., rings sharing adjacent pairs of carbon atoms) functional group.

In the present specification, "heterocyclic group" is a generic concept of a heteroaryl group, and may include at least one heteroatom selected from N, O, S, P, and Si instead of carbon (C) in a cyclic compound such as an aryl group, a cycloalkyl group, a fused ring thereof, or a combination thereof. When the heterocyclic group is a fused ring, the entire ring or each ring of the heterocyclic group may include one or more heteroatoms.

For example, "a heteroaryl group" may refer to an aryl group including at least one heteroatom selected from N, O, S, P, and Si. Two or more heteroaryl groups are linked by a sigma bond directly, or when the heteroaryl group includes two or more rings, the two or more rings may be fused. When the heteroaryl group is a fused ring, each ring may include one to three heteroatoms.

Specific examples of the heterocyclic group may include a pyridinyl group, a pyrimidinyl group, a pyrazinyl group, a pyridazinyl group, a triazinyl group, a quinolinyl group, an isoquinolinyl group, a quinazolinyl group, and the like.

More specifically, the substituted or unsubstituted C6 to C30 aryl group and/or the substituted or unsubstituted C2 to C30 heterocyclic group may be a substituted or unsubstituted phenyl group, a substituted or unsubstituted naphthyl group, a substituted or unsubstituted anthracenyl group, a substituted or unsubstituted phenanthrenyl group, a substituted or unsubstituted naphthacenyl group, a substituted or unsubstituted pyrenyl group, a substituted or unsubstituted biphenyl group, a substituted or unsubstituted p-terphenyl group, a substituted or unsubstituted m-terphenyl group, a substituted or unsubstituted o-terphenyl group, a substituted or unsubstituted chrysenyl group, a substituted or unsubstituted triphenylene group, a substituted or unsubstituted perylenyl group, a substituted or unsubstituted fluorenyl group, a substituted or unsubstituted indenyl group, a substituted or unsubstituted furanyl group, a substituted or unsubstituted thiophenyl group, a substituted or unsubstituted pyrrolyl group, a substituted or unsubstituted pyrazolyl group, a substituted or unsubstituted imidazolyl group, a substituted or unsubstituted triazolyl group, a substituted or unsubstituted oxazolyl group, a substituted or unsubstituted thiazolyl group, a substituted or unsubstituted oxadiazolyl group, a substituted or unsubstituted thiadiazolyl group, a substituted or unsubstituted pyridyl group, a substituted or unsubstituted pyrimidinyl group, a substituted or unsubstituted pyrazinyl group, a substituted or unsubstituted triazinyl group, a substituted or unsubstituted benzofuranyl group, a substituted or unsubstituted benzothiophenyl group, a substituted or unsubstituted benzimidazolyl group, a substituted or unsubstituted indolyl group, a substituted or unsubstituted quinolinyl group, a substituted or unsubstituted isoquinolinyl group, a substituted or unsubstituted quinazolinyl group, a substituted or unsubstituted quinoxalinyl group, a substituted or unsubstituted benzoquinolinyl group, a substituted or unsubstituted benzoisoquinolinyl group, a substituted or unsubstituted benzoquinazolinyl group, a substituted or unsubstituted naphthyridinyl group, a substituted or unsubstituted benzoxazinyl group, a substituted or unsubstituted benzthiazinyl group, a substituted or unsubstituted acridinyl group, a substituted or unsubstituted phenazinyl group, a substituted or unsubstituted phenothiazinyl group, a substituted or unsubstituted phenoxazinyl group, a substituted or unsubstituted dibenzofuranyl group, or a substituted or unsubstituted dibenzothiophenyl group, or combination thereof, but are not limited thereto.

In the present specification, hole characteristics refer to an ability to donate an electron to form a hole when an electric field is applied and that a hole formed in the anode may be easily injected into the light emitting layer and transported in the light emitting layer due to conductive characteristics according to a highest occupied molecular orbital (HOMO) level.

In addition, electron characteristics refer to an ability to accept an electron when an electric field is applied and that electron formed in the cathode may be easily injected into the light emitting layer and transported in the light emitting layer due to conductive characteristics according to a lowest unoccupied molecular orbital (LUMO) level.

Hereinafter, a composition for an organic optoelectronic device according to an embodiment is described.

The composition for an organic optoelectronic device according to an embodiment includes at least two types of hosts and dopants, and the host may include a first host compound having relatively strong electron characteristics and a second host compound having relatively strong hole characteristics.

The first host compound is a compound having relatively strong electron characteristics and represented by Chemical Formula 1.

[Chemical Formula 1]

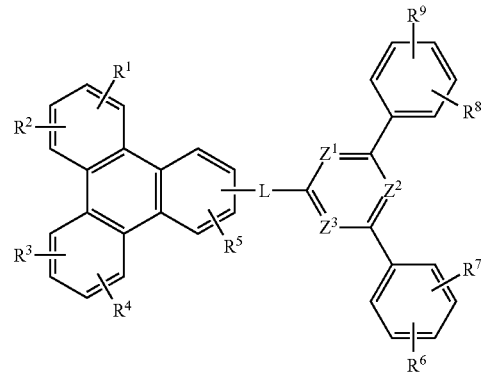

In Chemical Formula 1, $Z^1$ to $Z^3$ are each independently N or $CR^a$, at least two of $Z^1$ to $Z^3$ are N, L is a single bond, or a substituted or unsubstituted C6 to C18 arylene group, $R^a$ and $R^1$ to $R^9$ are each independently hydrogen, deuterium, a hydroxyl group, a thiol group, a cyano group, a substituted or unsubstituted C1 to C20 alkyl group, or a substituted or unsubstituted C6 to C18 aryl group, and $R^6$ to $R^9$ are each independently present or adjacent groups thereof are linked with each other to form a substituted or unsubstituted dibenzofuranyl group, or a substituted or unsubstituted dibenzothiophenyl group.

The "substituted" refers to replacement of at least one hydrogen by deuterium, a C1 to C10 alkyl group, or a C6 to C18 aryl group.

In one example of the present invention, the "substituted" refers to replacement of at least one hydrogen by deuterium, a C1 to C4 alkyl group, or a C6 to C12 aryl group. Specifically, it refers to replacement of at least one hydrogen by a C1 to C4 alkyl group, a phenyl group, a biphenyl group, a naphthyl group, a terphenyl group, or an anthracenyl group, for example replacement by a phenyl group, a biphenyl group, or a naphthyl group.

The first host compound may be represented as Chemical Formula 1A or Chemical Formula 1B according to a bonding position of the triphenylene group.

[Chemical Formula 1A]

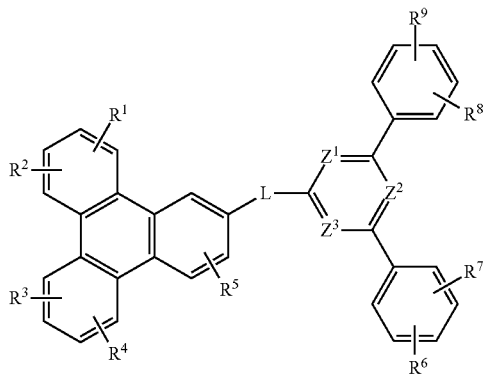

[Chemical Formula 1B]

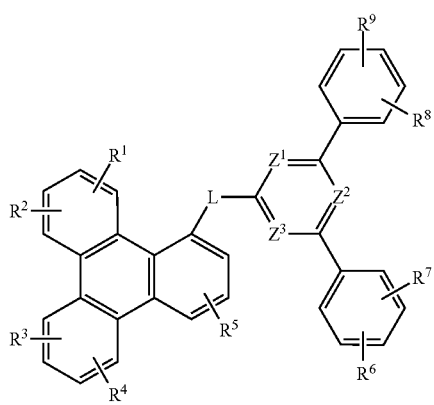

In Chemical Formulae 1A and 1B, $Z^1$ to $Z^3$, L and $R^1$ to $R^9$ are the same as described above.

The first host compound includes a triphenylene group and a 6-membered ring including at least two nitrogen atoms, i.e. a pyrimidinyl group or a triazinyl group.

The first host compound may have a structure capable of easily accepting electrons by including the pyrimidinyl group or the triazinyl group when an electric field is applied thereto and accordingly, a driving voltage of an organic optoelectronic device manufactured by applying the first host compound may be lowered.

In addition, the first host compound may have a bipolar structure by including the triphenylene structure capable of easily accepting holes and the nitrogen-containing 6-membered ring moiety capable of easily accepting electrons, thereby appropriately balancing hole and electron flows and thus, efficiency of the organic optoelectronic device manufactured by applying the first host compound may be improved.

In one example of the present invention, $Z^1$ to $Z^3$ are desirably all N.

In one example of the present invention, L may be a single bond, a substituted or unsubstituted phenylene group, a substituted or unsubstituted biphenylene group, or a substituted or unsubstituted terphenylene group, In a more specific example, L may be a single bond or one of substituted or unsubstituted linking groups of Group I.

[Group 1]

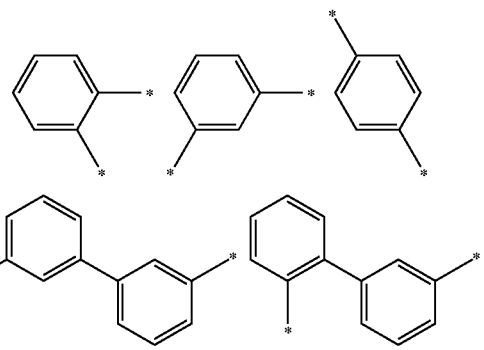

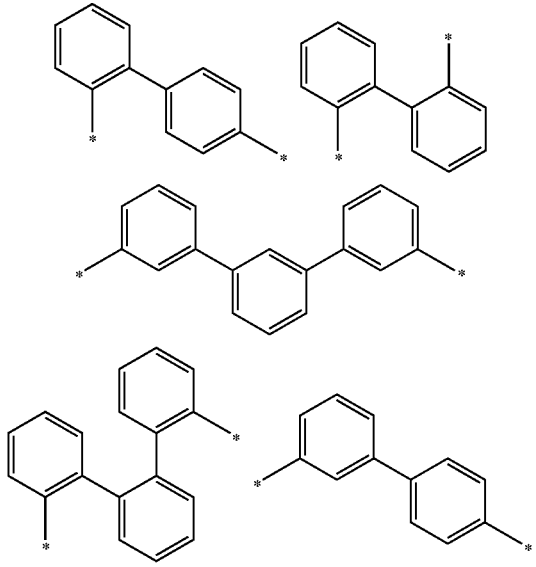

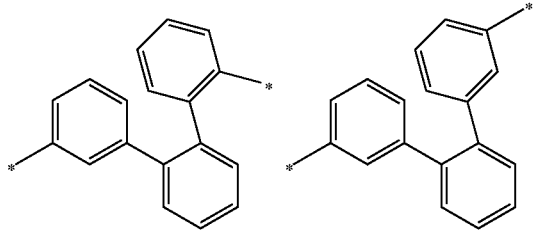

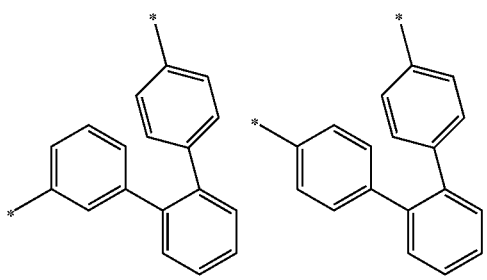
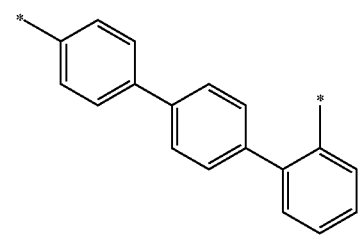
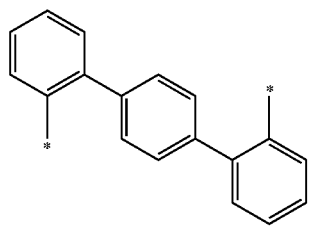
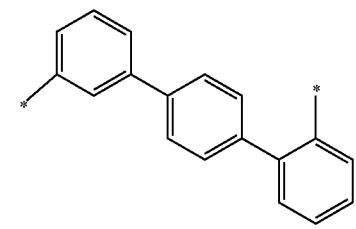
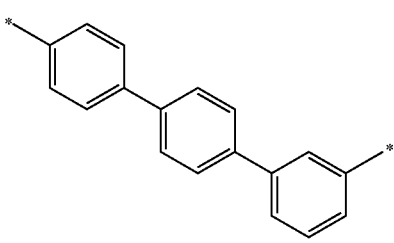
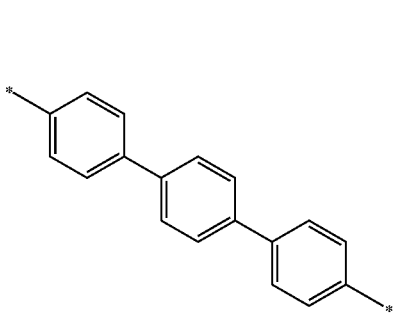

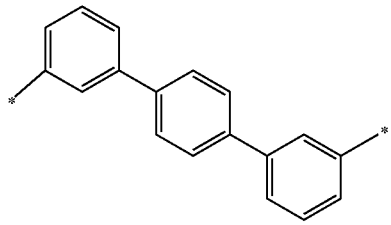

In Group I, * is a linking point.

In a more specific example, L may be a single bond or a substituted or unsubstituted para-phenylene group, a substituted or unsubstituted meta-phenylene group, a substituted or unsubstituted ortho-phenylene group, or a substituted or unsubstituted biphenylene group. In a more specific example, L may be a single bond or a para-phenylene group, or a meta-phenylene group.

In one example of the present invention, Chemical Formula 1 may be represented by Chemical Formula 1A and in a more specific example, it may be represented by one of Chemical Formula 1A-1, Chemical Formula 1A-2, Chemical Formula 1A-3, Chemical Formula 1A-4, and Chemical Formula 1A-5.

[Chemical Formula 1A-1]

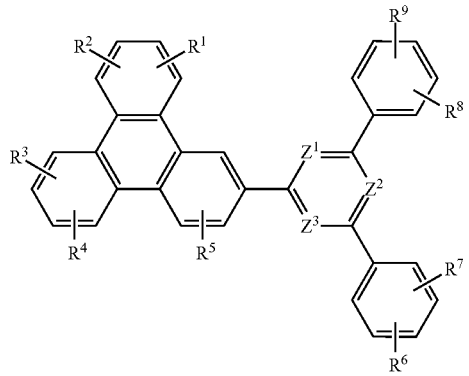

[Chemical Formula 1A-2]

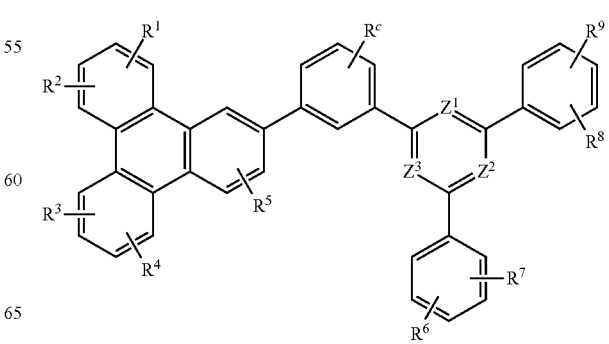

-continued

[Chemical Formula 1A-3]

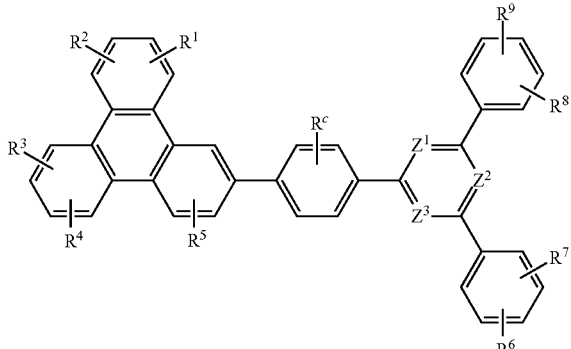

[Chemical Formula 1A-4]

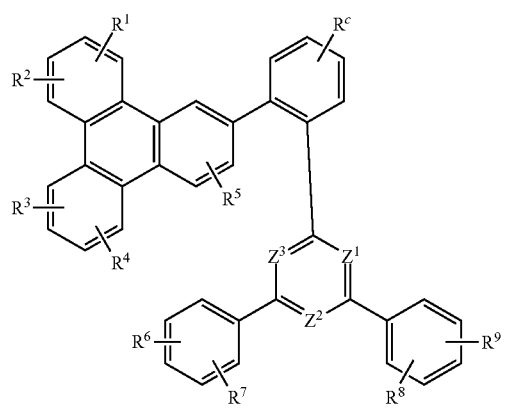

[Chemical Formula 1A-5]

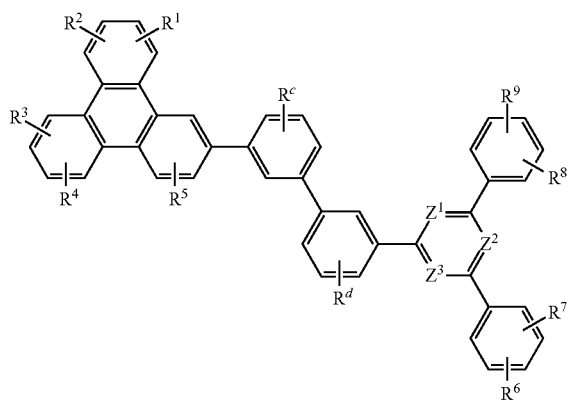

In Chemical Formulae 1A-1 to 1A-5, $Z^1$ to $Z^3$ and $R^1$ to $R^9$ are the same as described above.

In the most specific example of the present invention, Chemical Formula 1 may be represented by one of Chemical Formula 1A-1, Chemical Formula 1A-2, and Chemical Formula 1 A-3.

On the other hand, in one example of the present invention, the 6-membered ring including $Z^1$ to $Z^3$ may be a substituted or unsubstituted pyrimidinyl group, or a substituted or unsubstituted triazinyl group, and in the most specific example, the 6-membered ring including $Z^1$ to $Z^3$ may be a substituted or unsubstituted triazinyl group and may be, for example represented by one of Chemical Formula 1A-a, Chemical Formula 1A-b1, Chemical Formula 1A-b2, Chemical Formula 1B-a, Chemical Formula 1B-b1, and Chemical Formula 1B-b2.

[Chemical Formula 1A-a]

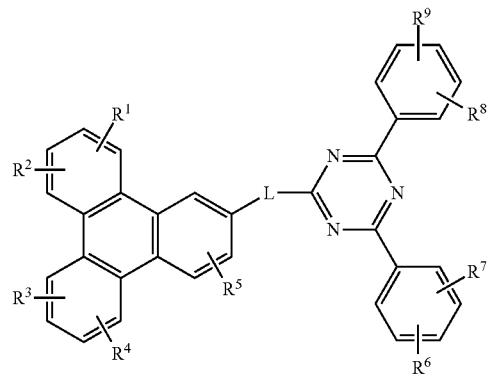

[Chemical Formula 1A-b1]

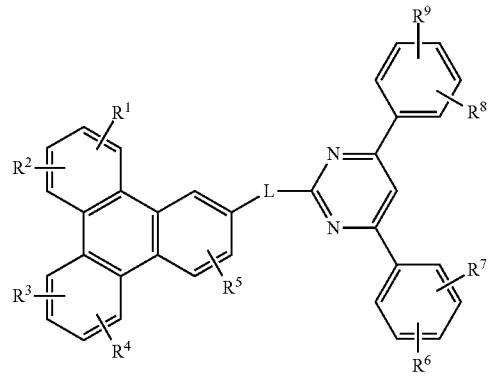

[Chemical Formula 1A-b2]

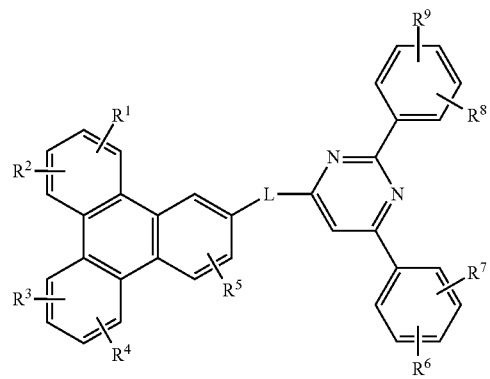

[Chemical Formula 1B-a]

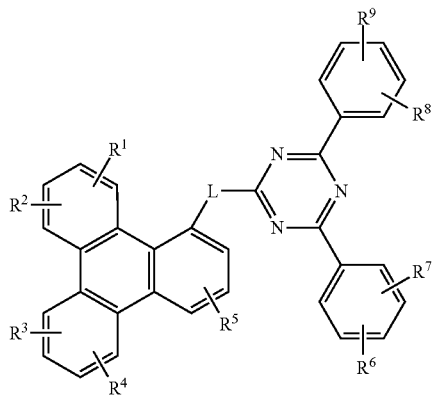

[Group 1]

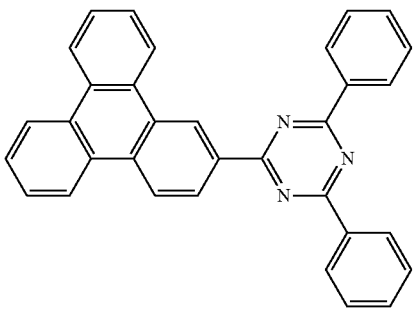

A-1

[Chemical Formula 1B-b1]

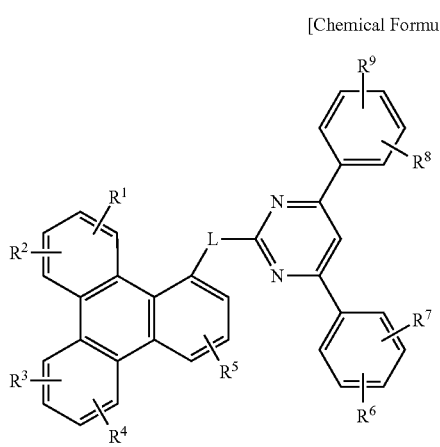

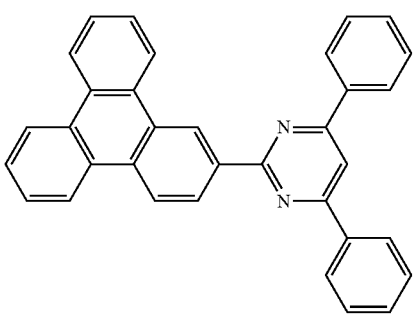

A-2

[Chemical Formula 1B-b2]

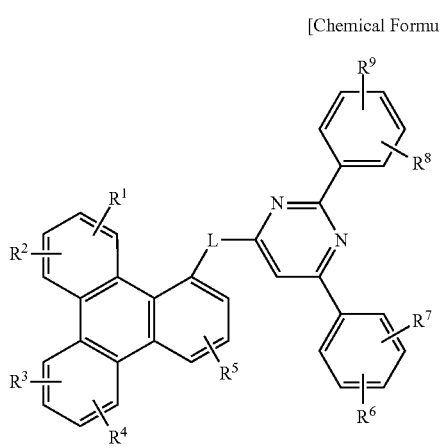

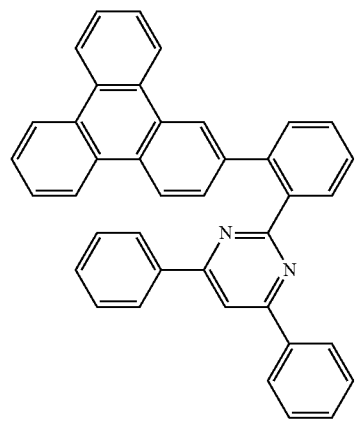

A-3

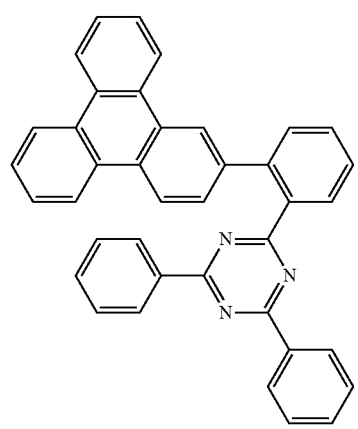

A-4

In Chemical Formula 1A-a, Chemical Formula 1A-b1, Chemical Formula 1A-b2, Chemical Formula 1B-a, Chemical Formula 1B-b1, and Chemical Formula 1B-b2, L and $R^1$ to $R^9$ are the same as described above.

In addition, in the most specific example of the present invention, Chemical Formula 1 may be represented by Chemical Formula 1A-a and in this case, L may be a single bond or a substituted or unsubstituted phenylene group.

The first compound for an organic optoelectronic device may be for example one of compounds of Group 1, but is not limited thereto.

A-5
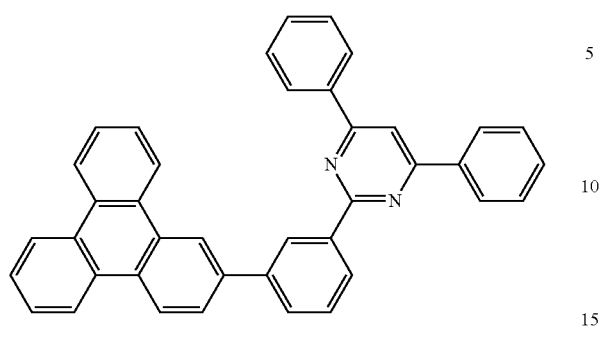
A-6
A-9
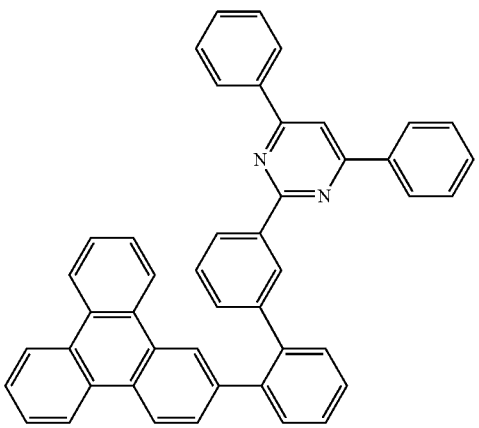
A-10
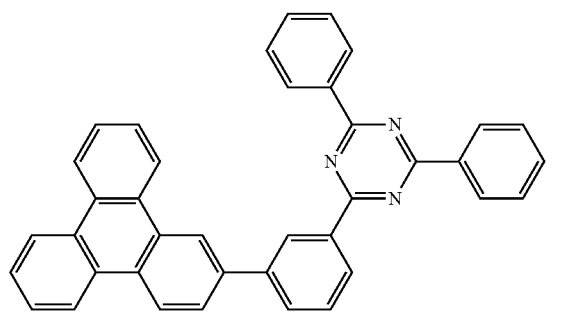
A-7
A-11
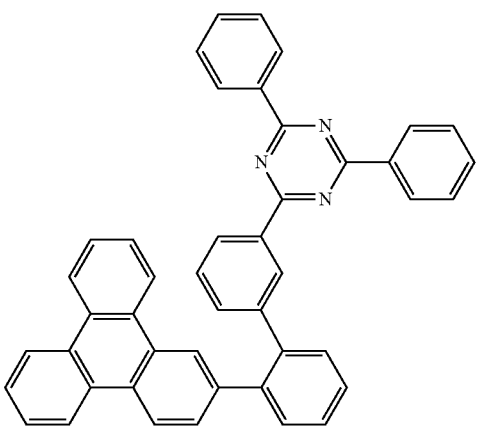
A-8
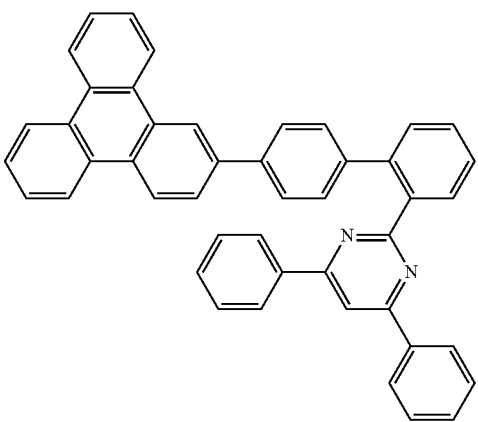

A-12
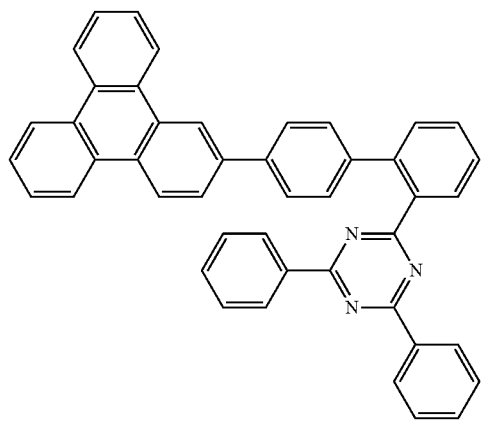
A-13
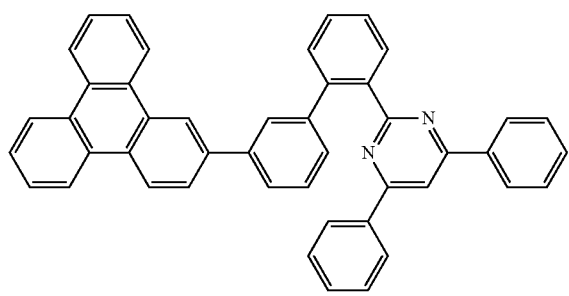
A-14
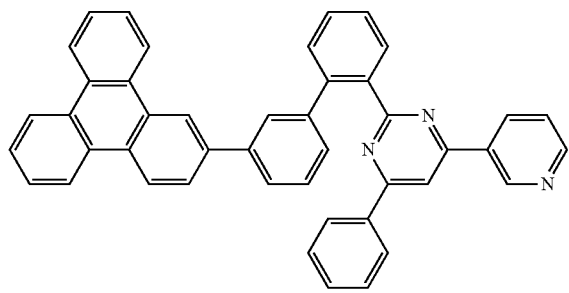
A-15
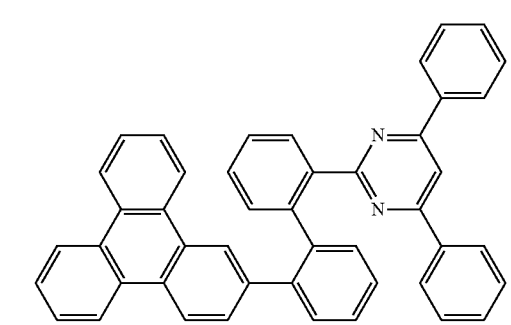
A-16
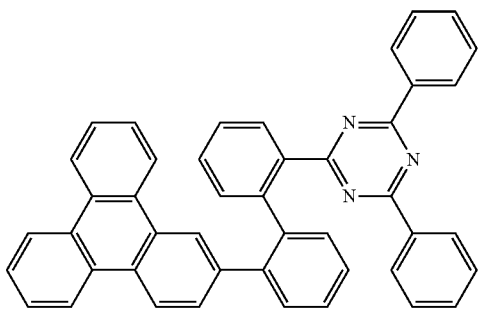
A-17
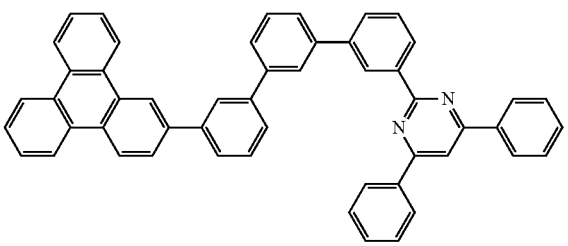
A-18
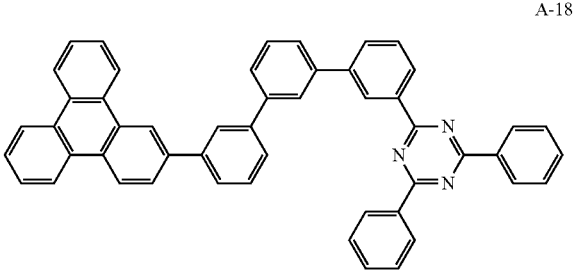
A-19
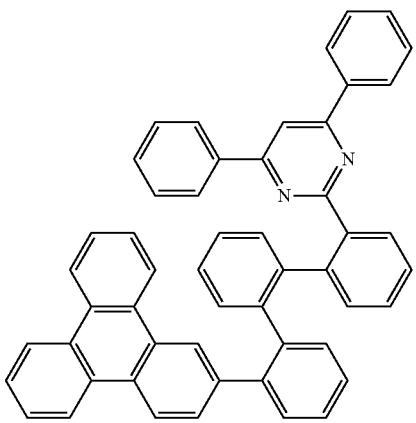

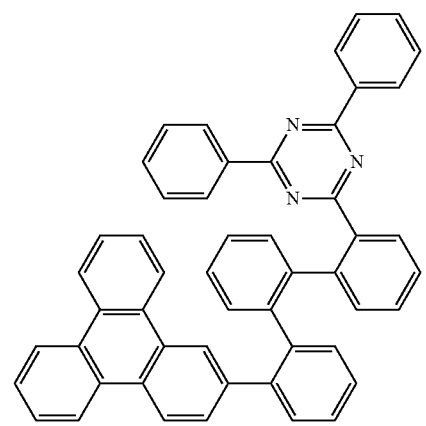
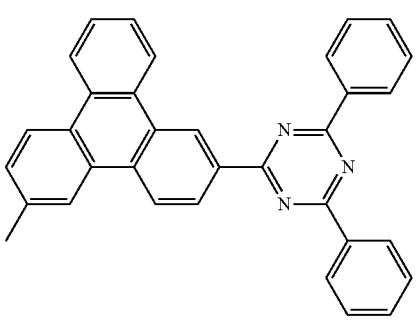
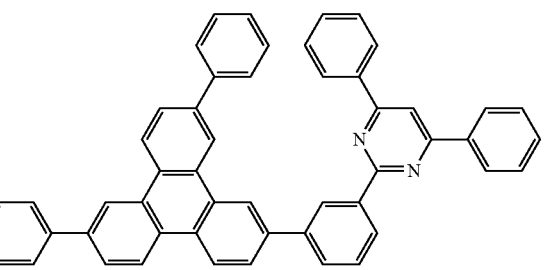

A-28
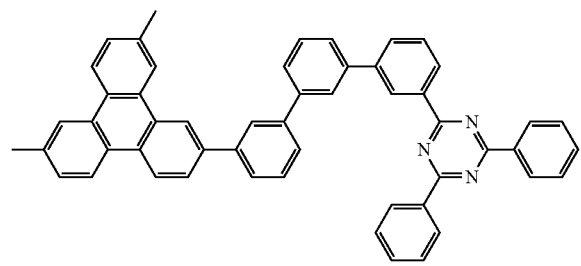
A-29
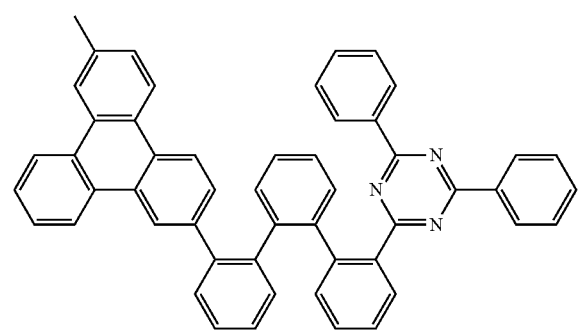
A-30
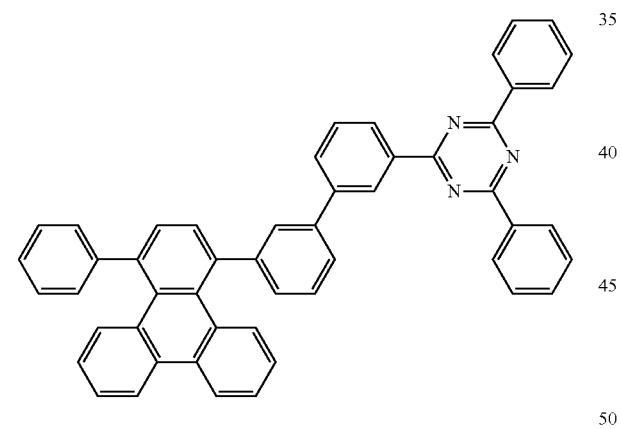
A-31
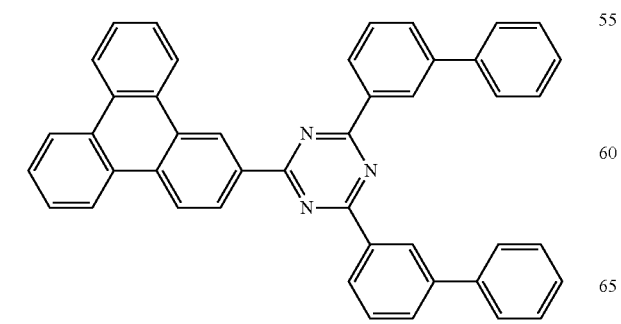
A-32
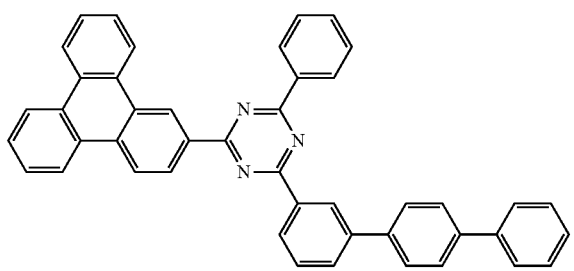
A-33
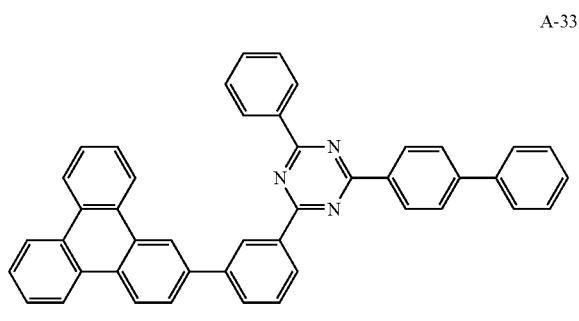
A-34
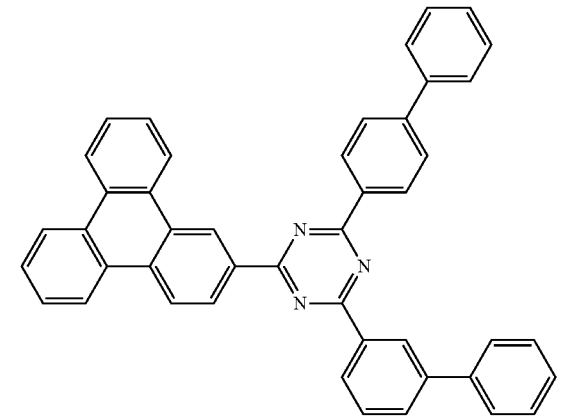
A-35
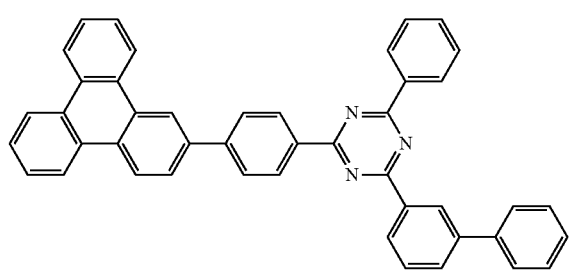

A-36
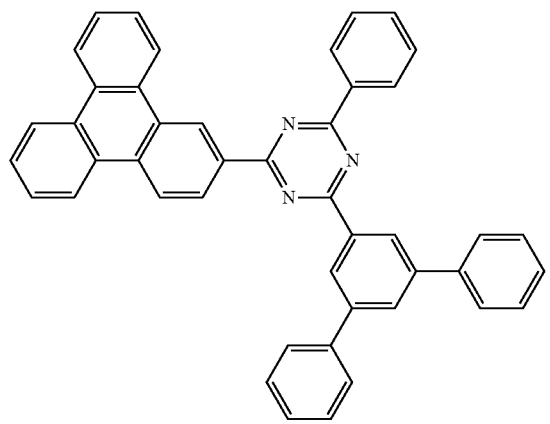
A-37
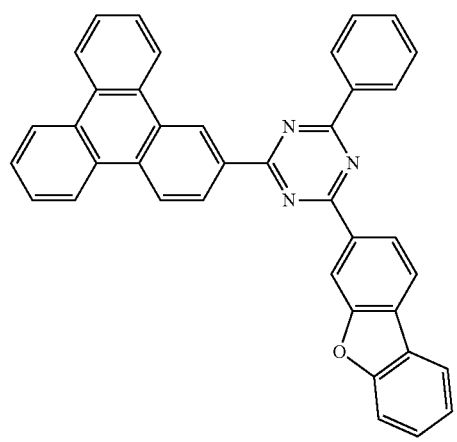
A-38
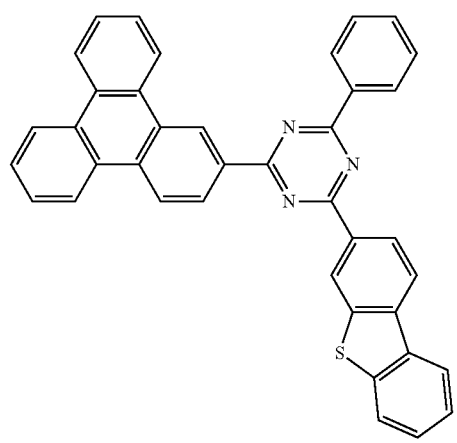
A-39
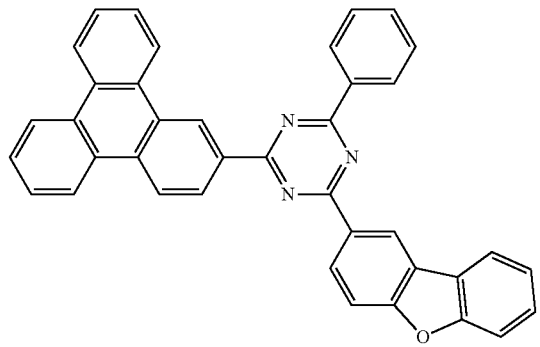
A-40
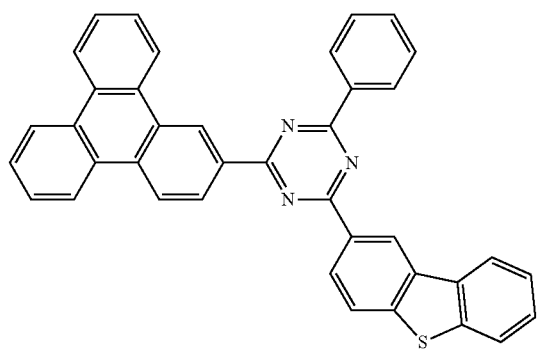
A-41
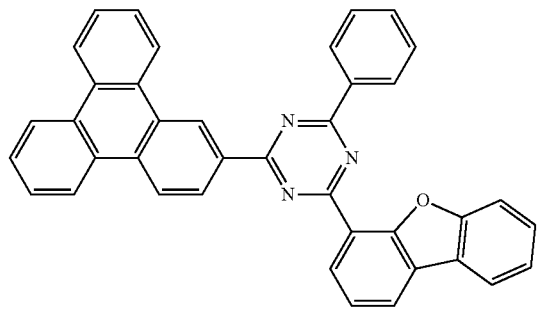
A-42
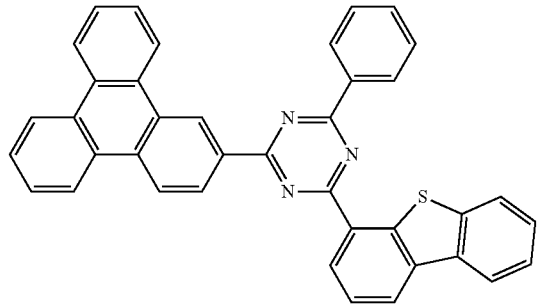

A-43
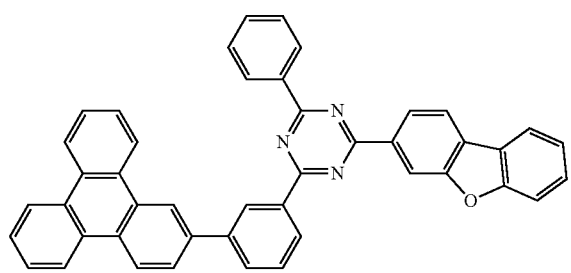
A-44
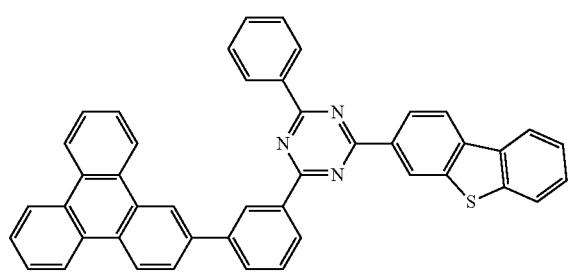
A-45
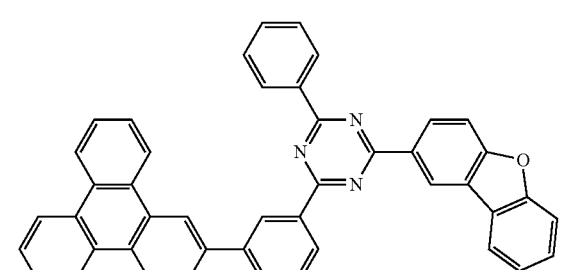
A-46
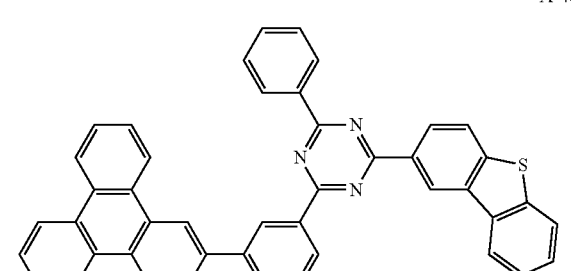
A-47
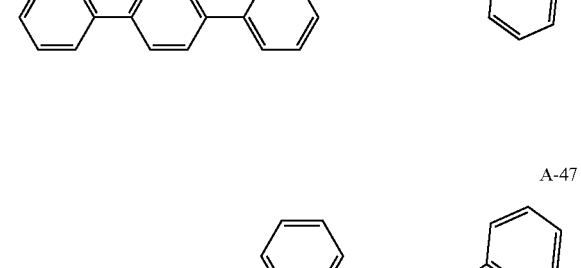
A-48
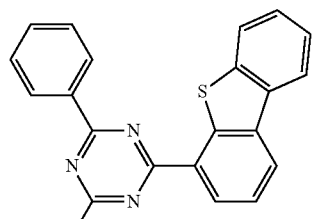
A-49
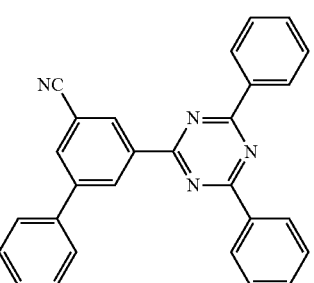
A-50
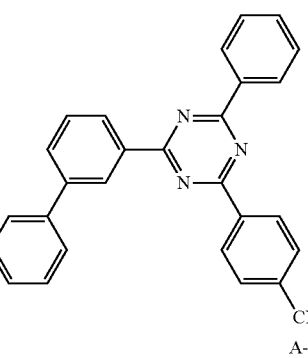
A-51
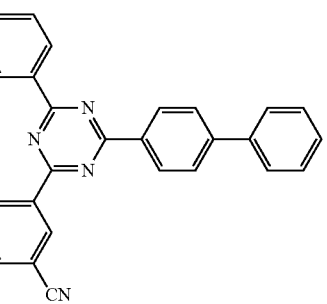
A-52
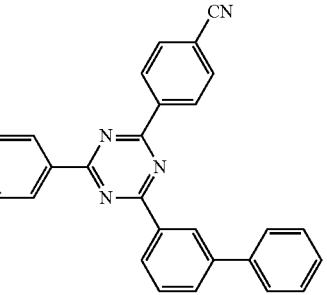

A-53

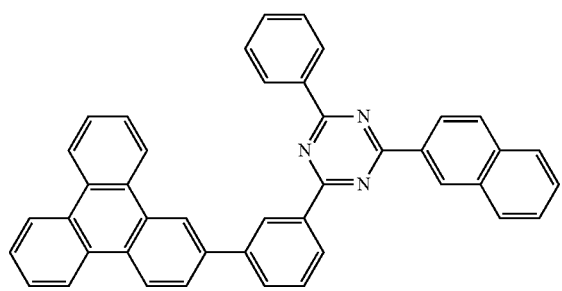

A-54

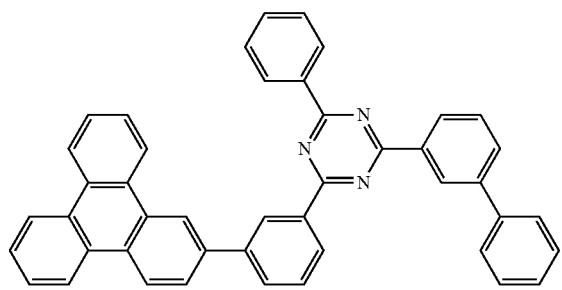

A-55

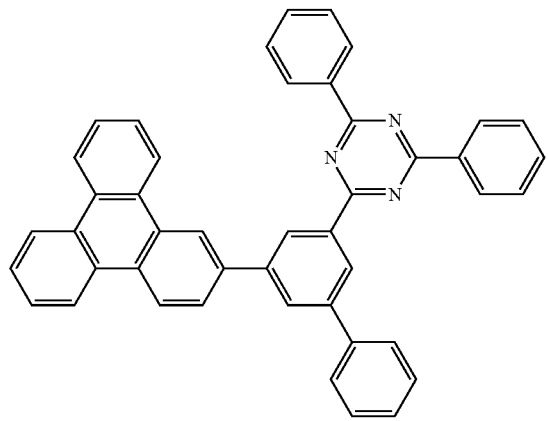

The second host compound is a compound having relatively strong hole characteristics and is represented by a combination of Chemical Formula 2 and Chemical Formula 3A, or a combination of Chemical Formula 2 and Chemical Formula 3B.

[Chemical Formula 2]

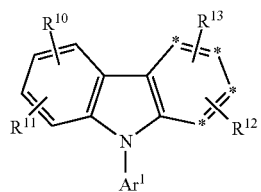

[Chemical Formula 3A]

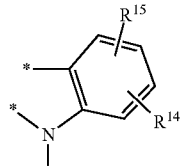

[Chemical Formula 3B]

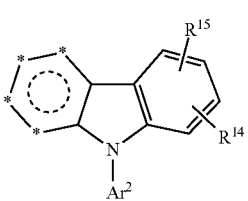

In Chemical Formula 2, Chemical Formula 3A, and Chemical Formula 3B, $Ar^1$ and $Ar^2$ are each independently a substituted or unsubstituted C6 to C30 aryl group, at least one of $Ar^1$ and $Ar^2$ is a substituted or unsubstituted C12 to C30 aryl group, adjacent two "*" of Chemical Formula 2 are linked with "*" of Chemical Formula 3A or adjacent two "*" of Chemical Formula 3B and remaining "*" of Chemical Formula 2 not linked with Chemical Formula 3A and Chemical Formula 3B and remaining "*" of Chemical Formula 3B not linked with Chemical Formula 2 are C or $CR^b$, $R^b$ and $R^{10}$ to $R^{15}$ are each independently hydrogen, deuterium, a substituted or unsubstituted C1 to C20 alkyl group, or a substituted or unsubstituted C6 to C18 aryl group, and $R^b$ and $R^{10}$ to $R^{15}$ are each independently present or adjacent groups are linked with each other to form a substituted or unsubstituted aliphatic monocyclic ring, aliphatic polycyclic ring, aromatic monocyclic ring, aromatic polycyclic ring, heteroaromatic monocyclic ring or heteroaromatic polycyclic ring.

For example, adjacent groups of $R^b$ and $R^{10}$ to $R^{15}$ may be linked with each other to form a phenylene ring and for example the second compound for an organic optoelectronic device by the combination of Chemical Formula 2 and Chemical Formula 3A may include one of moieties of Group II.

[Group II]

B-I

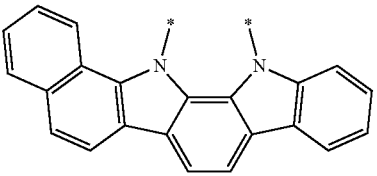

B-II

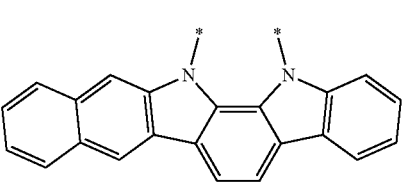

B-III
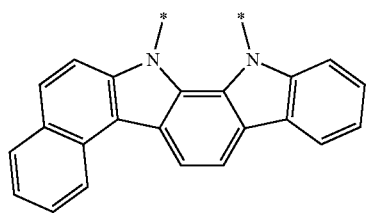
B-IV
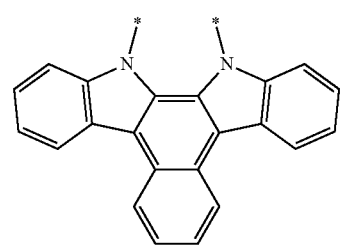
C-I
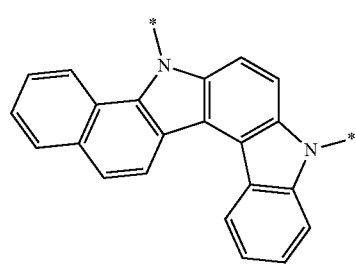
C-II
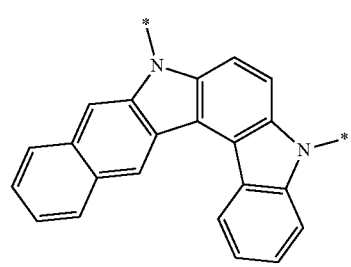
C-III
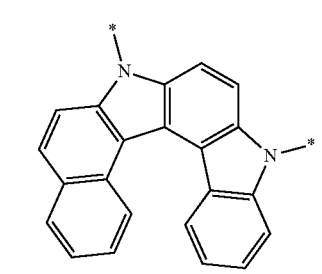
C-IV
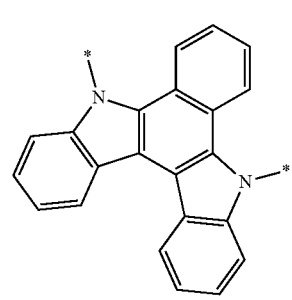
D-I
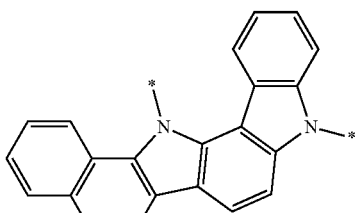
D-II
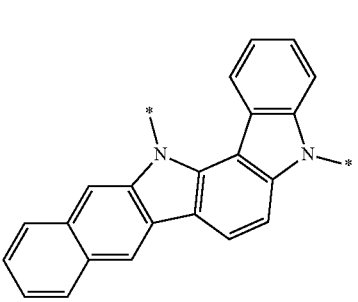
D-III
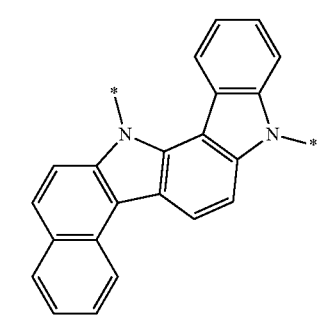
D-IV
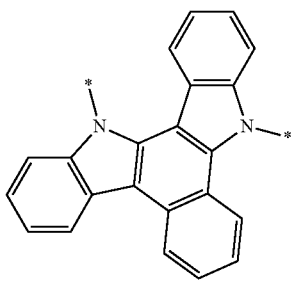
D-V
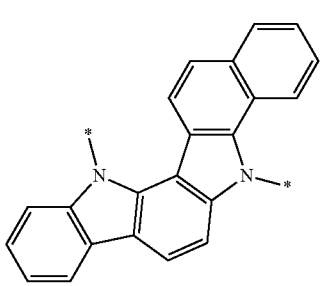

D-VI

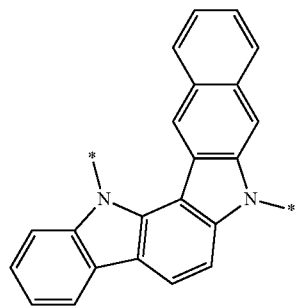

D-VII

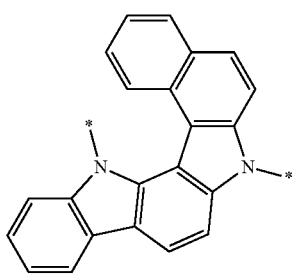

E-1

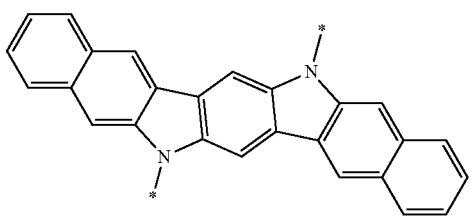

"Substituted" of Chemical Formula 2, Chemical Formula 3A, and Chemical Formula 3B refers to replacement of at least one hydrogen by deuterium, a C1 to C20 alkyl group, or a C6 to C30 aryl group.

In one example of the present invention, the "substituted" refers to replacement of at least one hydrogen by deuterium, a C1 to C4 alkyl group, or a C6 to C12 aryl group. Specifically, it may refer to replacement of at least one hydrogen by a C1 to C4 alkyl group, a phenyl group, a biphenyl group, a naphthyl group, a terphenyl group, an anthracenyl group, a fluorenyl group, a phenanthrenyl group, or a triphenylene group, for example a phenyl group, a biphenyl group, a naphthyl group, a terphenyl group, or an anthracenyl group.

The second compound for an organic optoelectronic device is a compound having relatively strong hole characteristics and has easy hole injection and high hole mobility. It is used together with the first compound in a light emitting layer for an organic optoelectronic device to balance the charge and to increase stability, and thereby a driving voltage, luminous efficiency, and life-span characteristics may be improved. In addition, a ratio of the second compound for an organic optoelectronic device having hole characteristics and the first compound for an organic optoelectronic device may be adjusted and thereby charge mobility may be controlled.

In one example of the present invention, the second host compound may be for example represented by one of Chemical Formula 2A, Chemical Formula 2B, Chemical Formula 2C, Chemical Formula 2D, Chemical Formula 2E, Chemical Formula 2F, Chemical Formula 2G, and Chemical Formula 2H according to a fusion point of Chemical Formula 2 and Chemical Formula 3A, or a fusion point of Chemical Formula 2 and Chemical Formula 3B.

[Chemical Formula 2A]

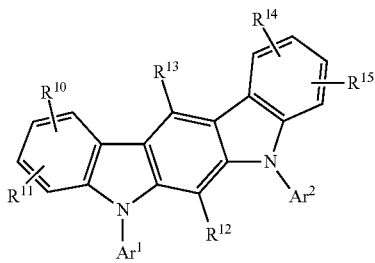

[Chemical Formula 2B]

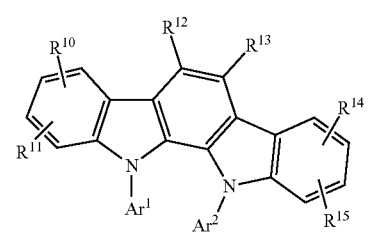

[Chemical Formula 2C]

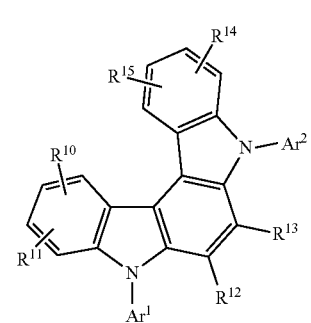

[Chemical Formula 2D]

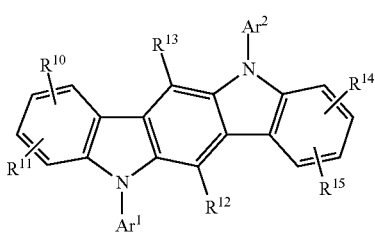

[Chemical Formula 2E]

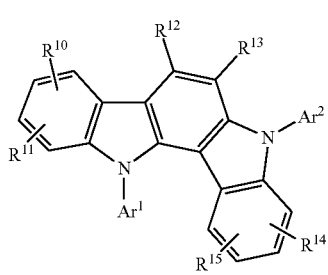

-continued

[Chemical Formula 2F]

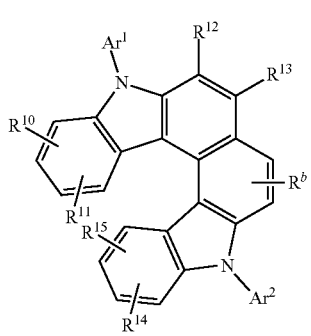

[Chemical Formula 2G]

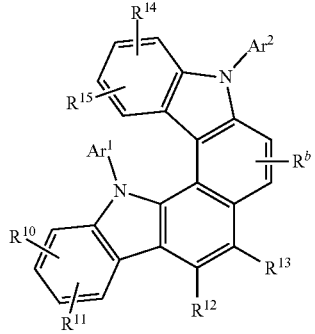

[Chemical Formula 2H]

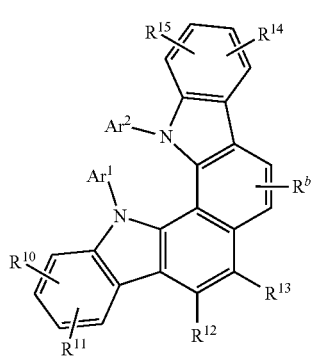

In Chemical Formula 2A to Chemical Formula 2H,
Ar$^1$, Ar$^2$ and R$^{10}$ to R$^{15}$ are the same as described above.

In a more specific example, the second compound for an organic optoelectronic device may be represented by Chemical Formula 2C or Chemical Formula 2E, and may be more specifically Chemical Formula 2C.

On the other hand, in one example of the present invention, Ar$^1$ may be a substituted or unsubstituted phenyl group, a substituted or unsubstituted biphenyl group, a substituted or unsubstituted terphenyl group or a substituted or unsubstituted naphthyl group and Ar$^2$ may be a substituted or unsubstituted biphenyl group, a substituted or unsubstituted terphenyl group, a substituted or unsubstituted naphthyl group, a substituted or unsubstituted anthracenyl group, a substituted or unsubstituted phenanthrenyl group, or a substituted or unsubstituted triphenylenyl group.

In a more specific example, Ar$^1$ may be a substituted or unsubstituted phenyl group, or a substituted or unsubstituted biphenyl group and Ar$^2$ may be a substituted or unsubstituted biphenyl group, a substituted or unsubstituted terphenyl group, or a substituted or unsubstituted triphenylenyl group.

Herein, in Chemical Formula 2A to Chemical Formula 2H, at least one of Ar$^1$ and the Ar$^2$ may be a substituted or unsubstituted naphthyl group.

The second compound for an organic optoelectronic device may be for example a compound of Group 2, but is not limited thereto.

[Group 2]

B-1

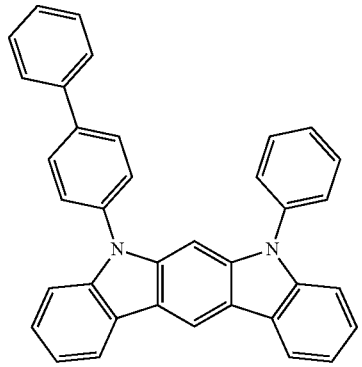

B-2

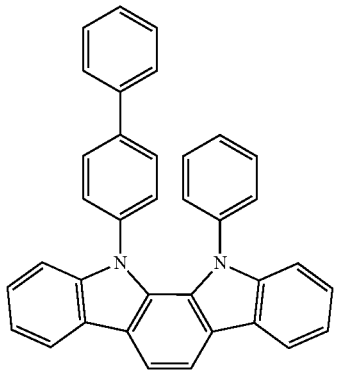

B-3

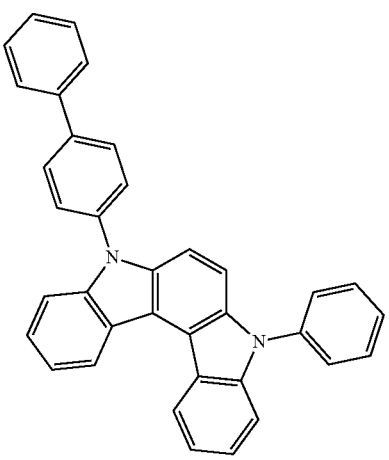

B-4
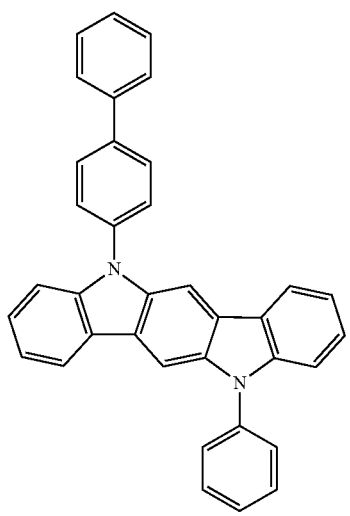
B-5
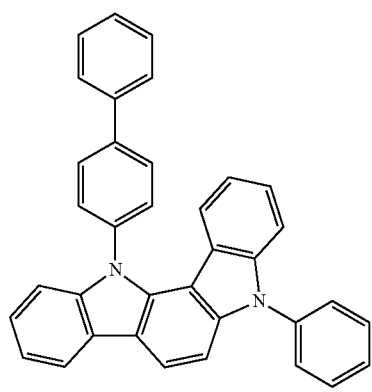
B-6
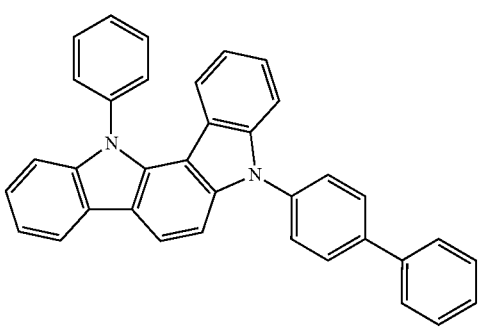
B-7
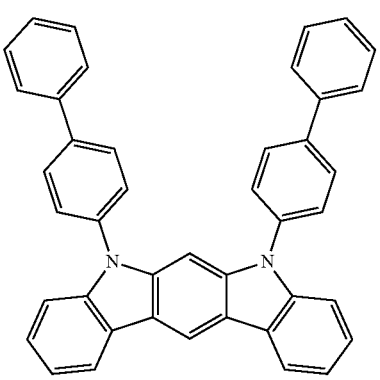
B-8
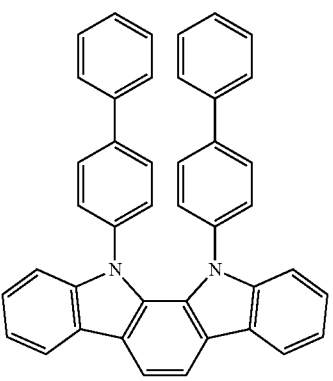
B-9
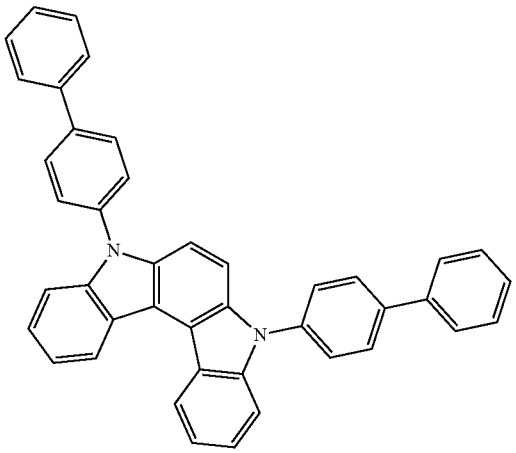
B-10
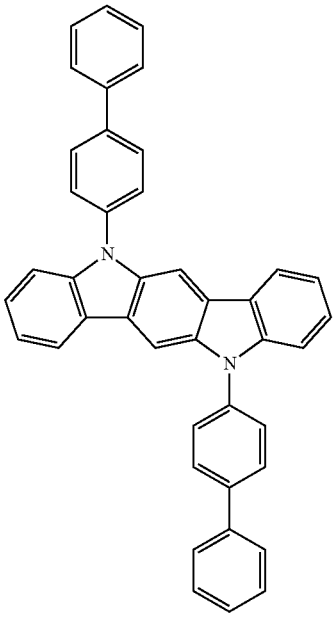

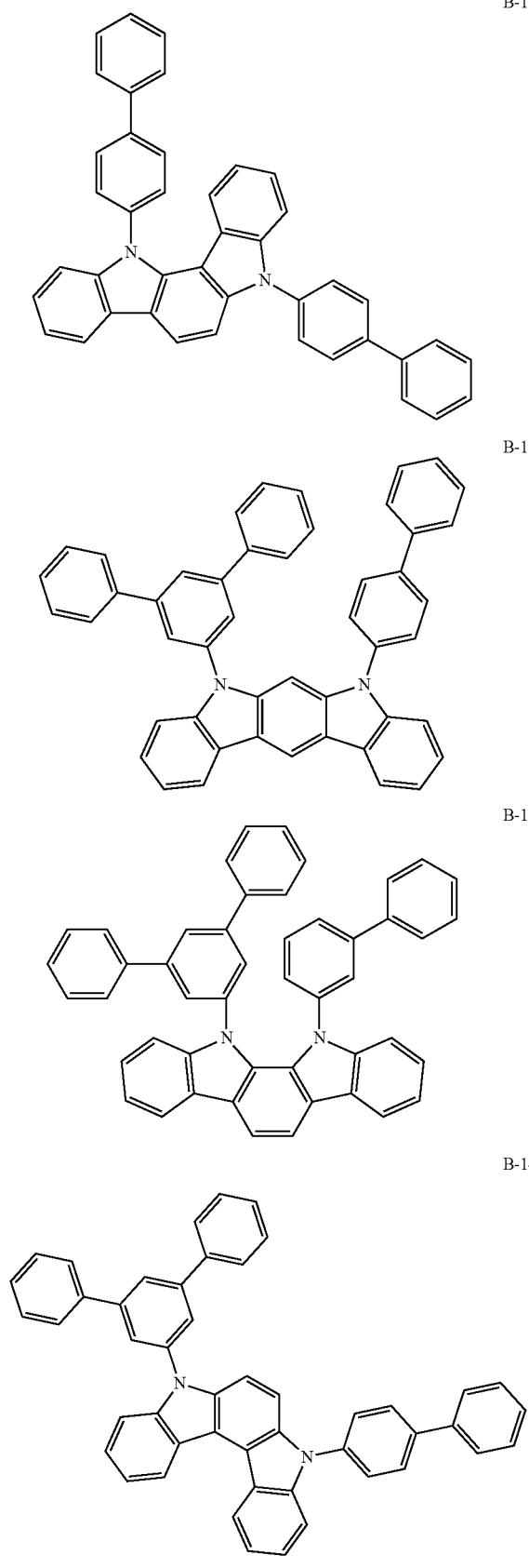
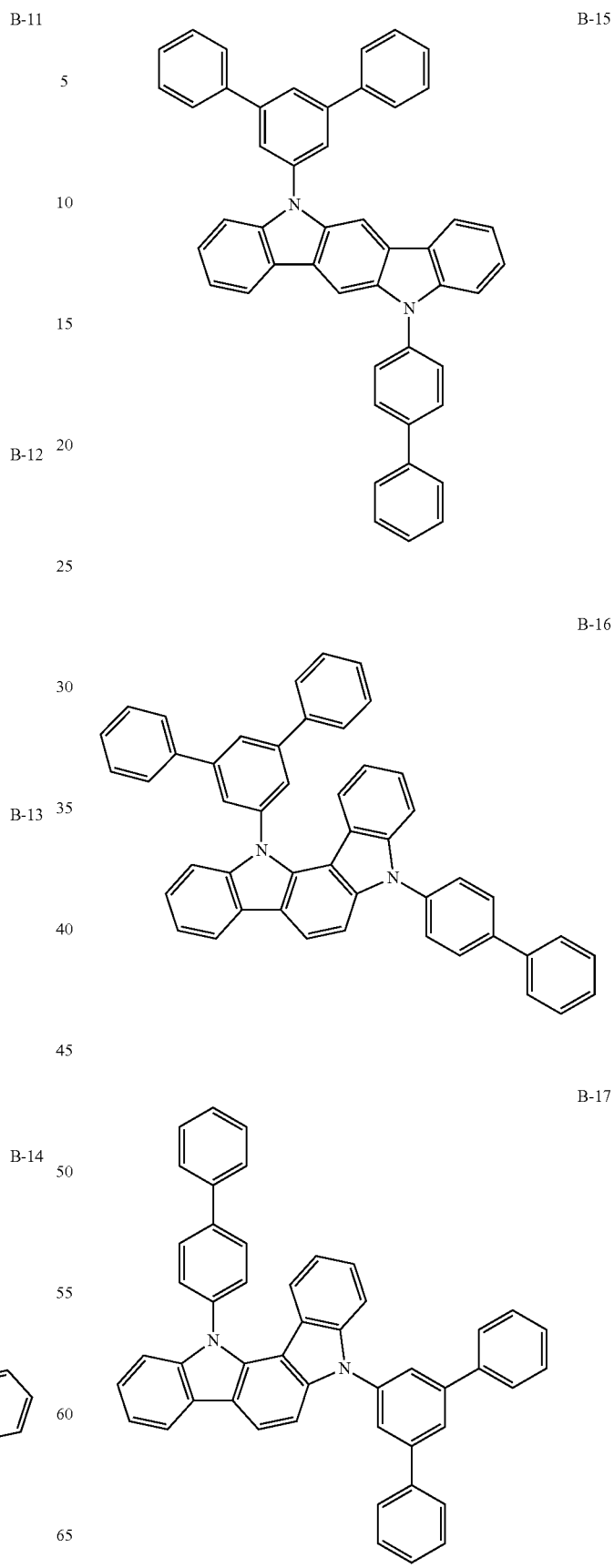

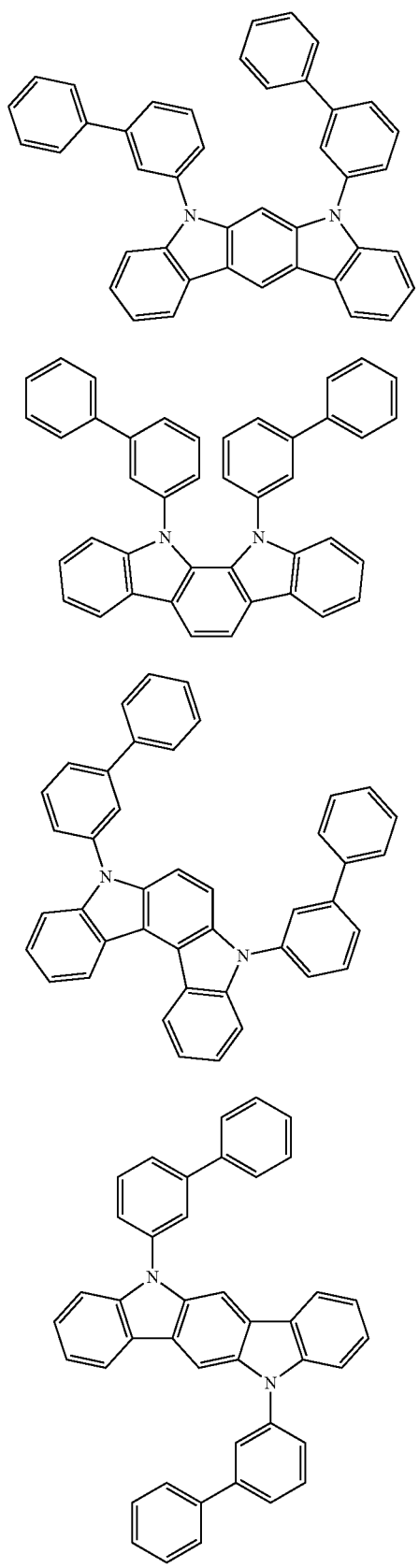
B-18
B-19
B-20
B-21
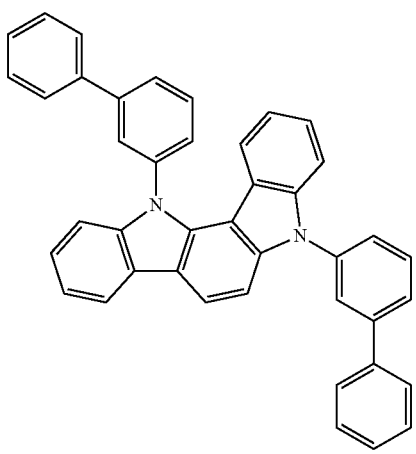
B-22
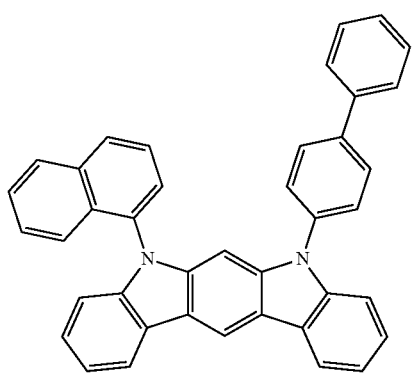
B-23
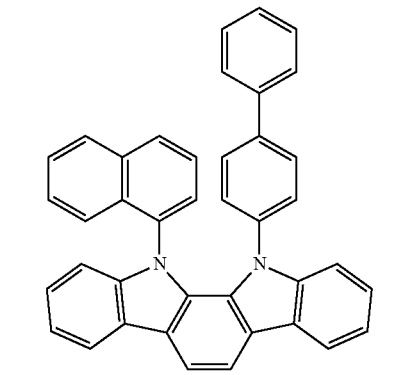
B-24
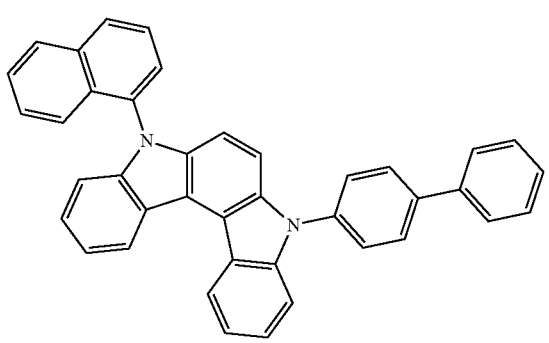
B-25

B-26
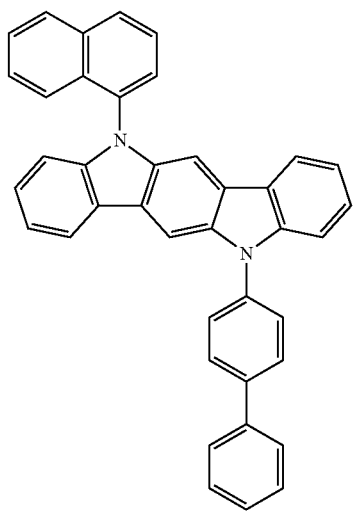
B-27
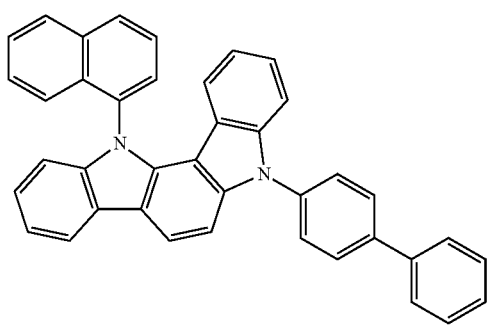
B-28
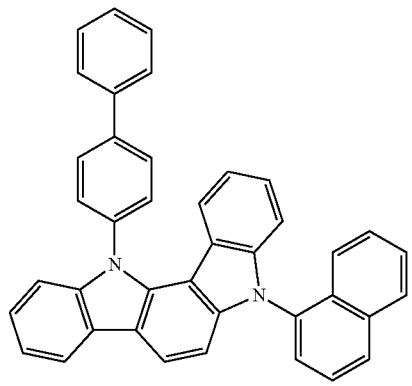
B-29
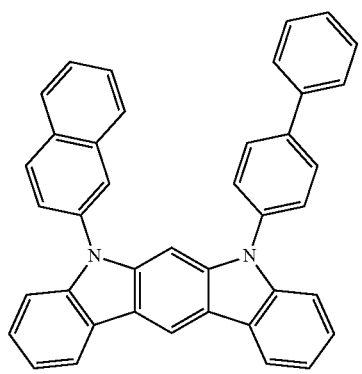
B-30
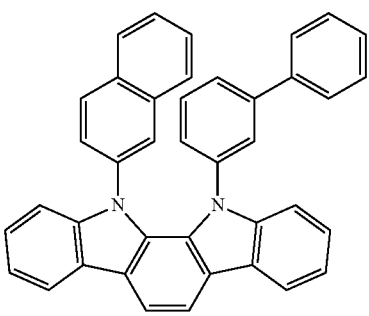
B-31
B-32
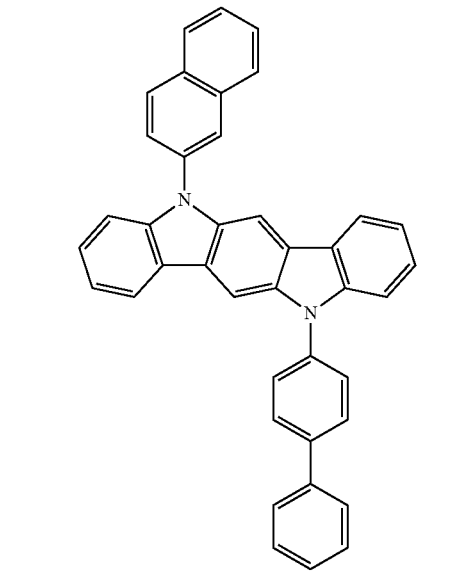

B-33
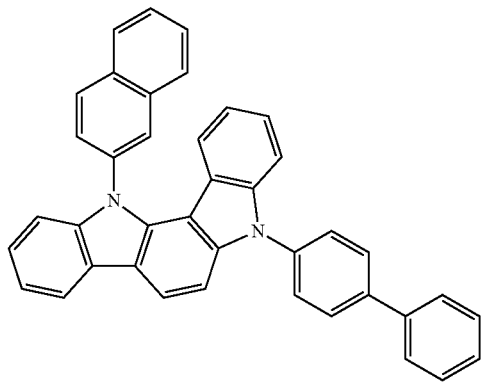
B-34
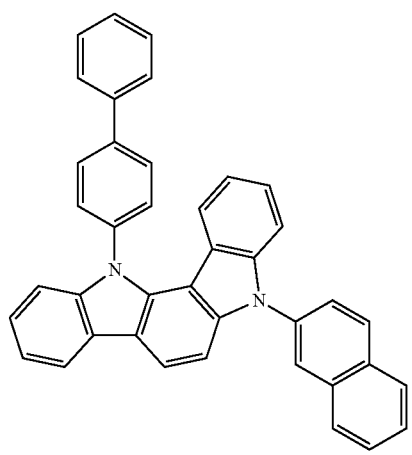
B-35
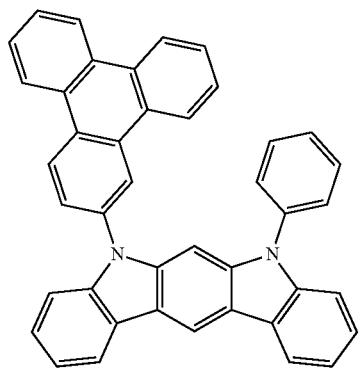
B-36
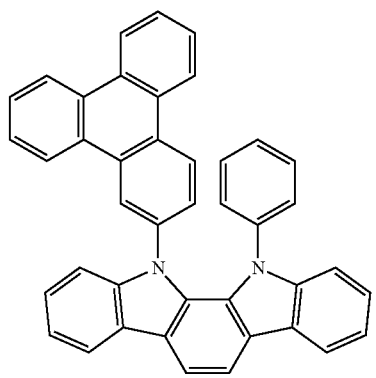
B-37
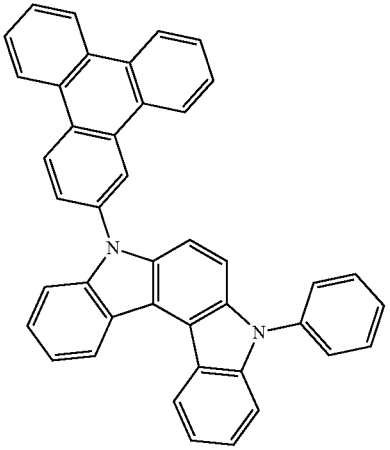
B-38
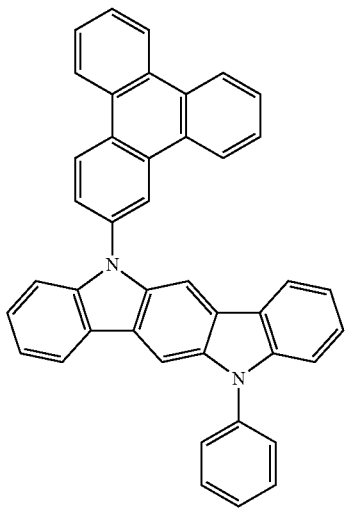
B-39
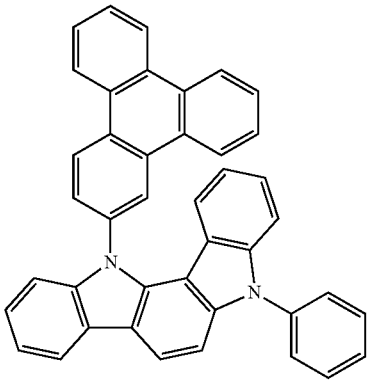

B-40
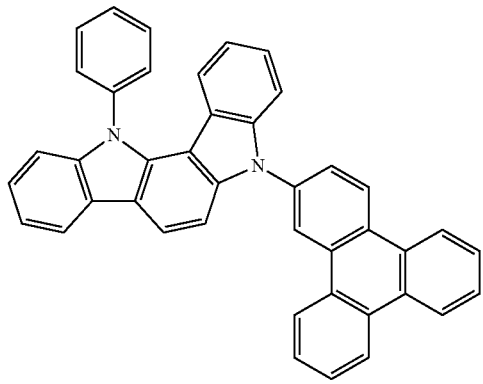
B-41
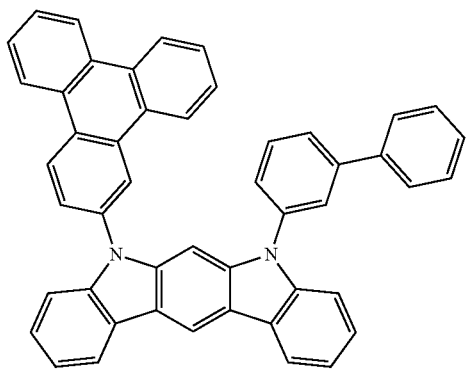
B-42
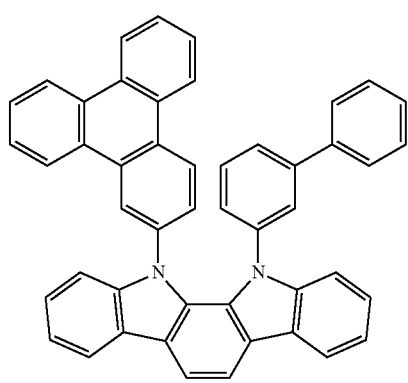
B-43
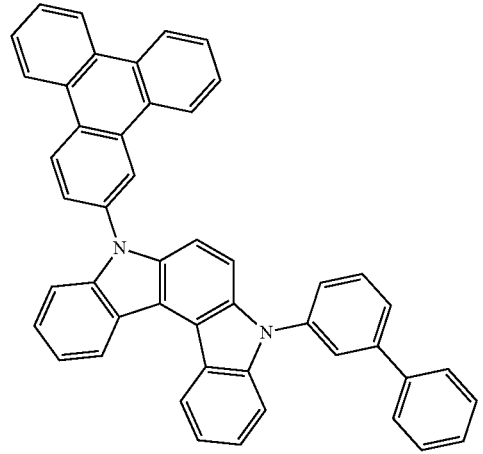
B-44
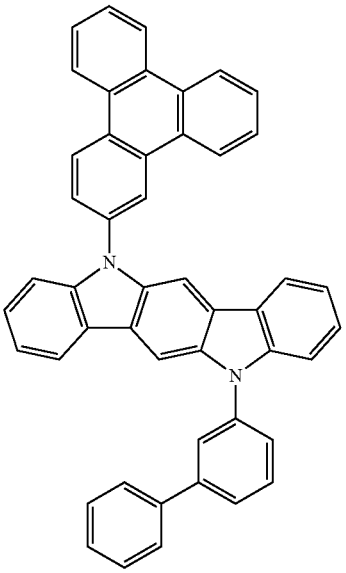
B-45
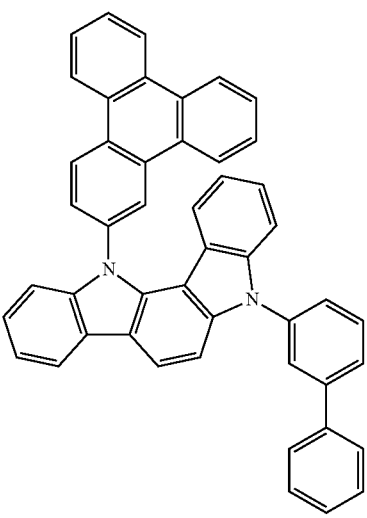
B-46
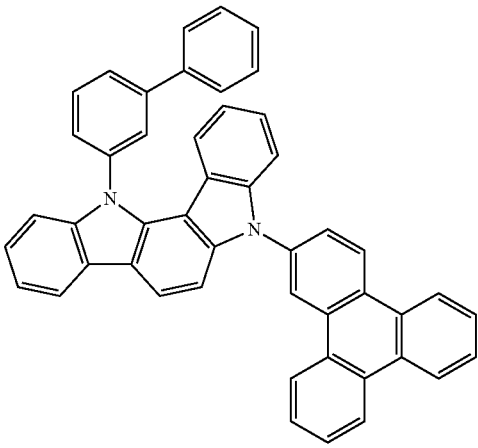

B-47
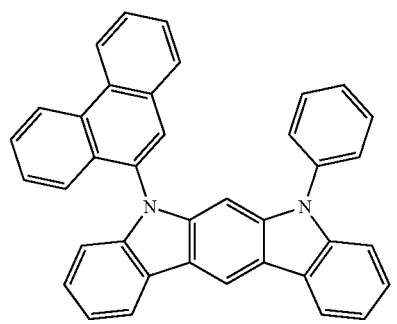
B-48
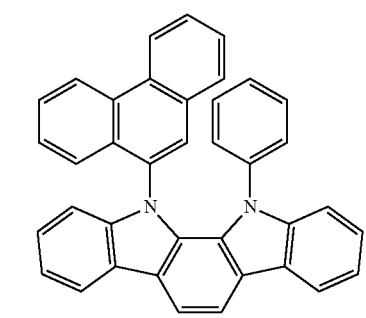
B-49
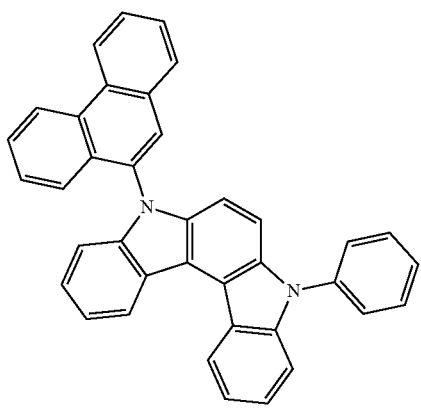
B-50
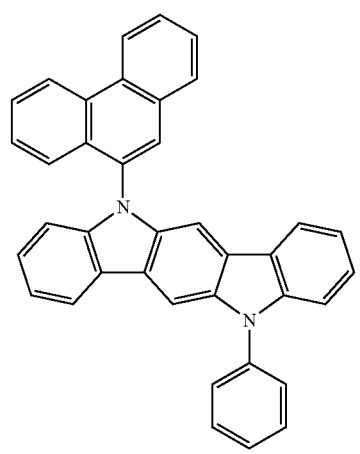
B-51
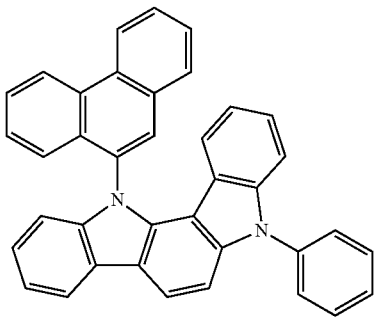
B-52
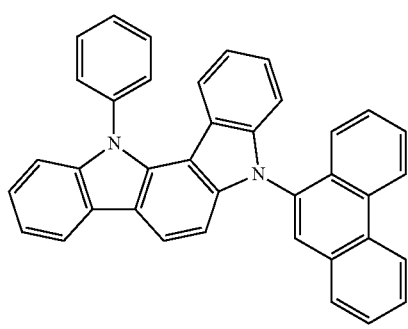
B-53
B-54
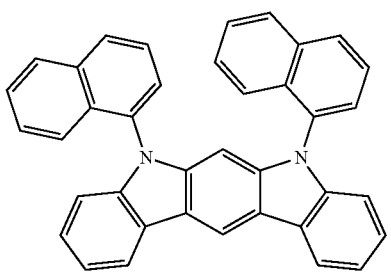
B-55
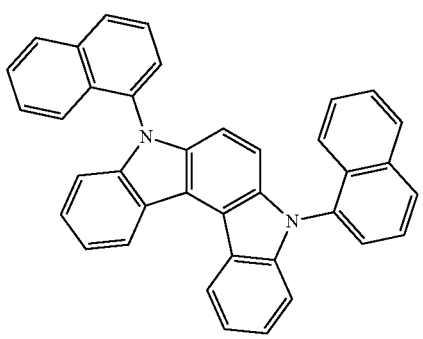

B-56
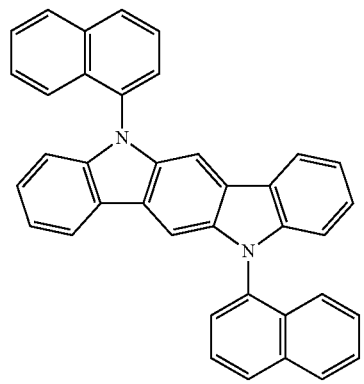
B-60
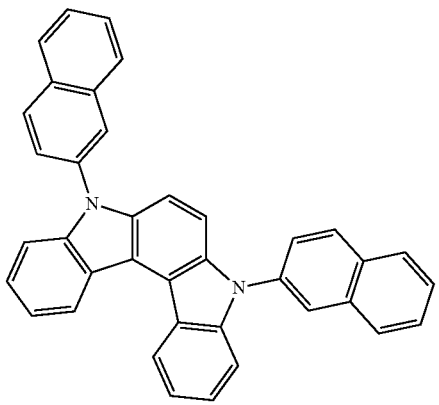
B-57
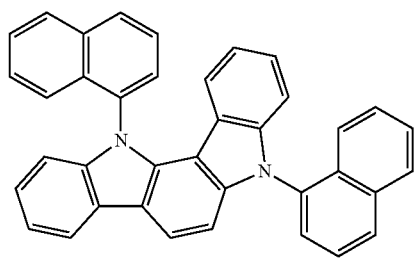
B-61
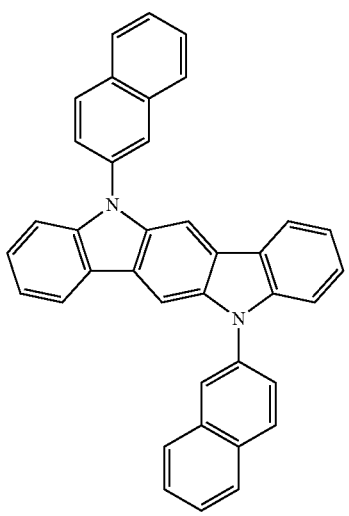
B-58
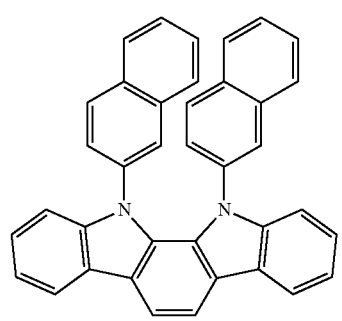
B-59
B-62
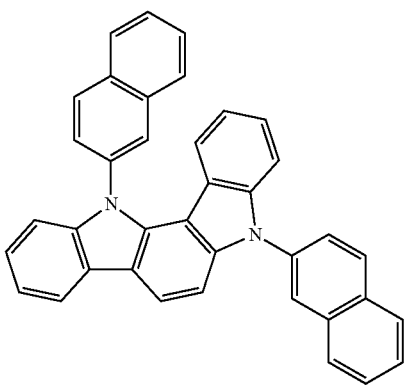

B-63
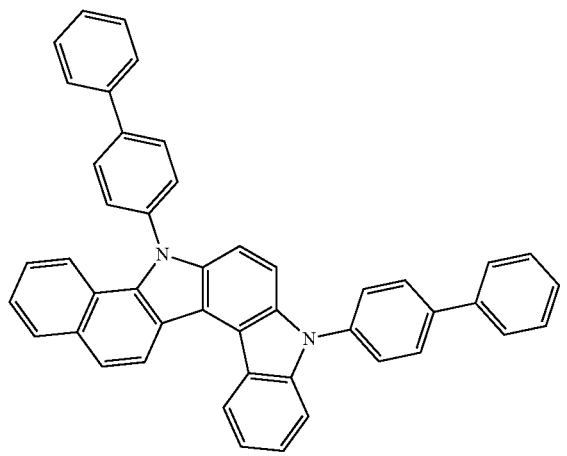
B-64
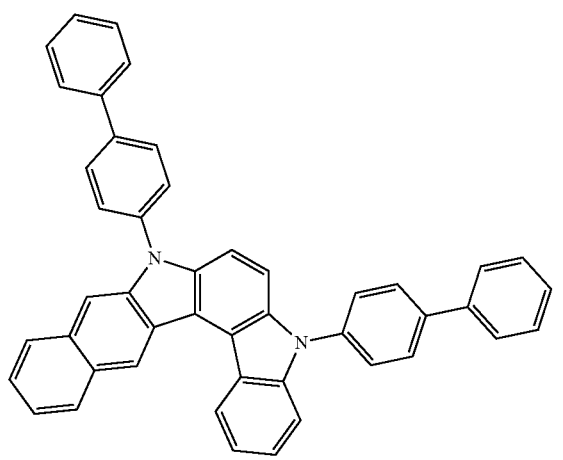
B-65
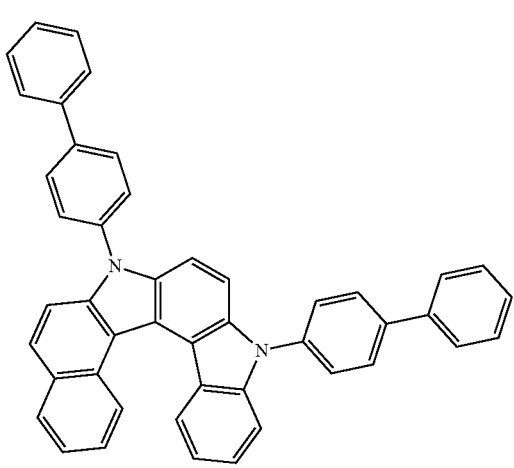
B-66
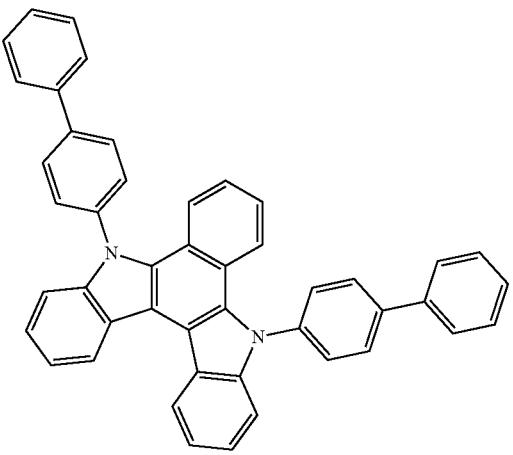
B-67
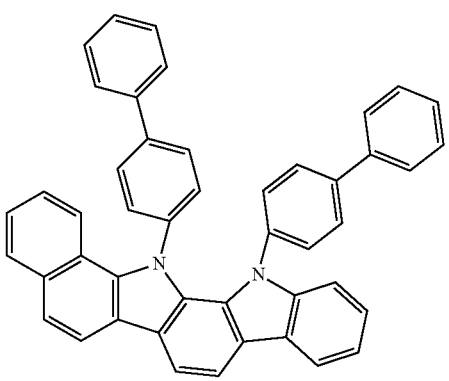
B-68
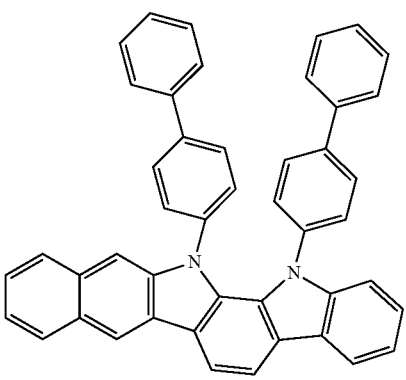
B-69
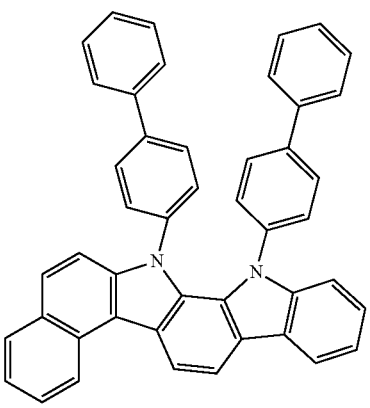

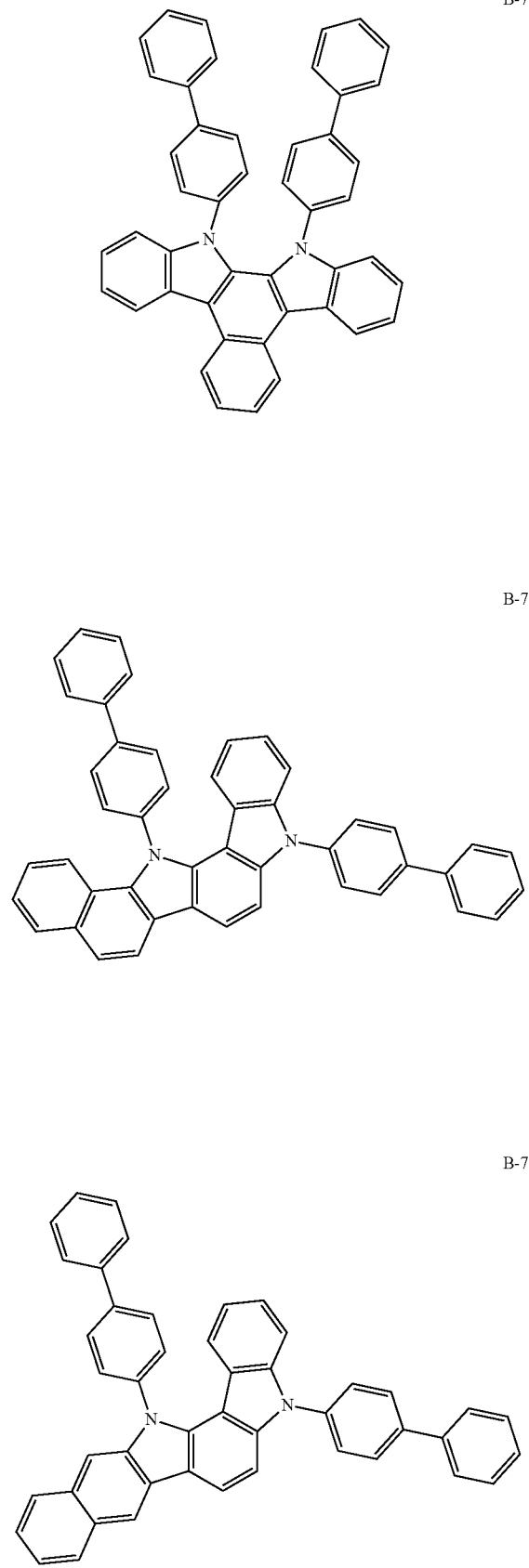
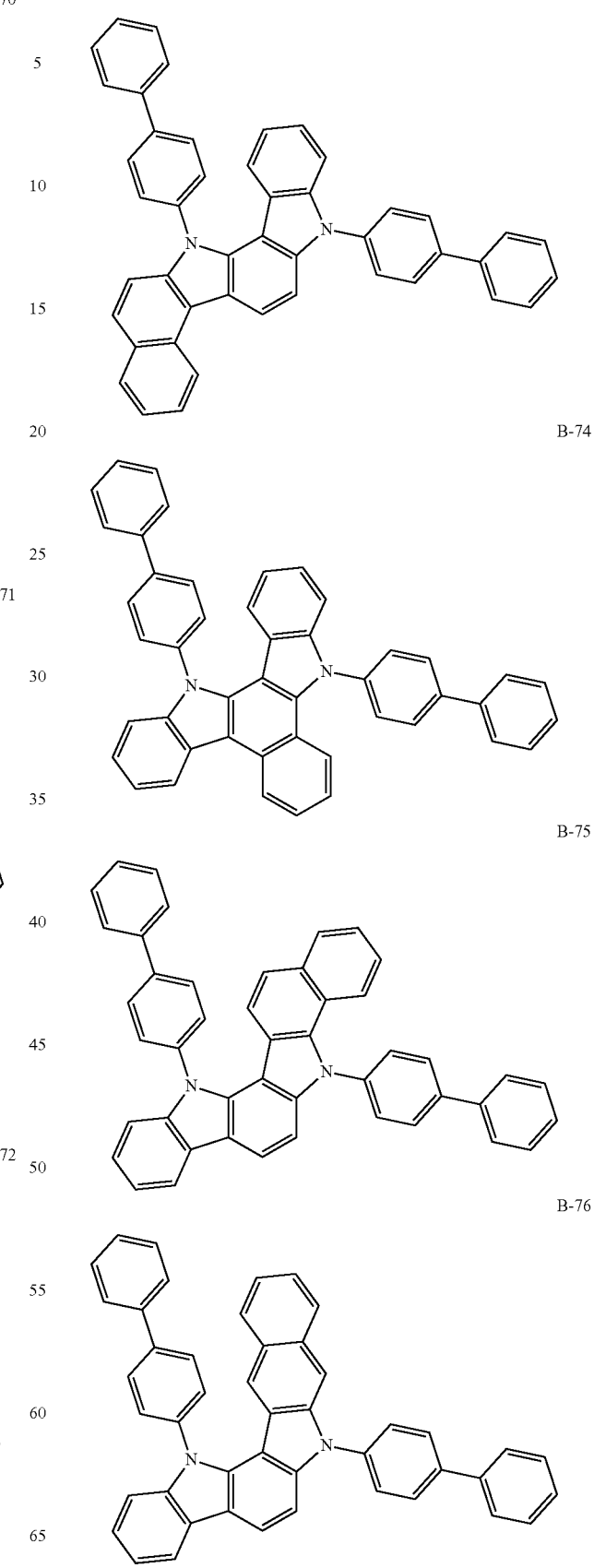

B-77
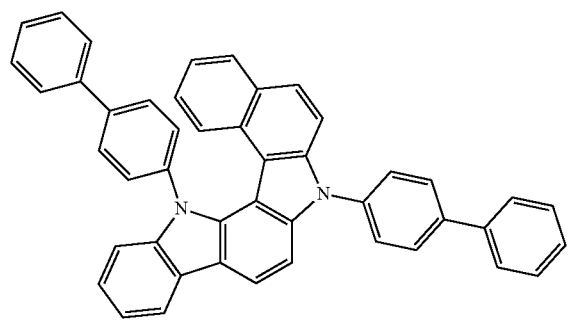
B-78
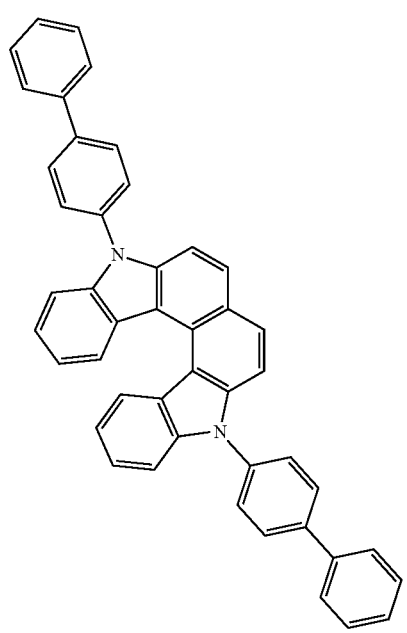
B-79
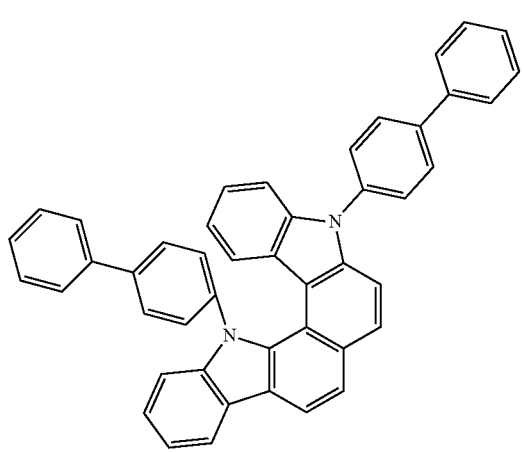
B-80
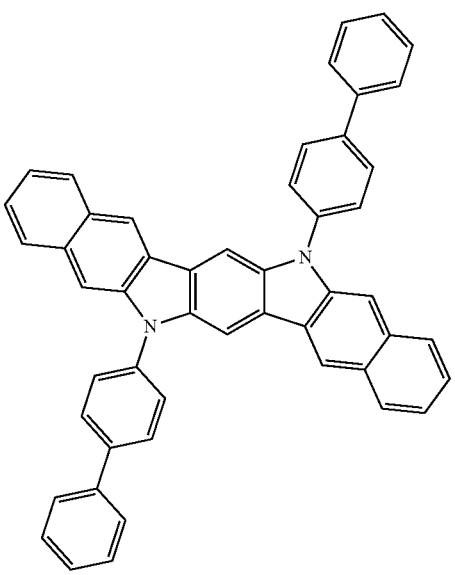
B-81
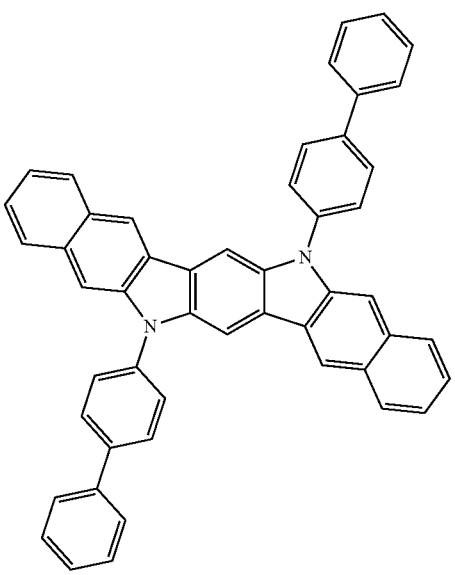
B-82
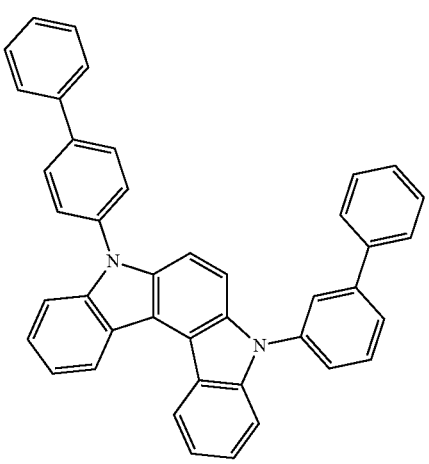

B-83
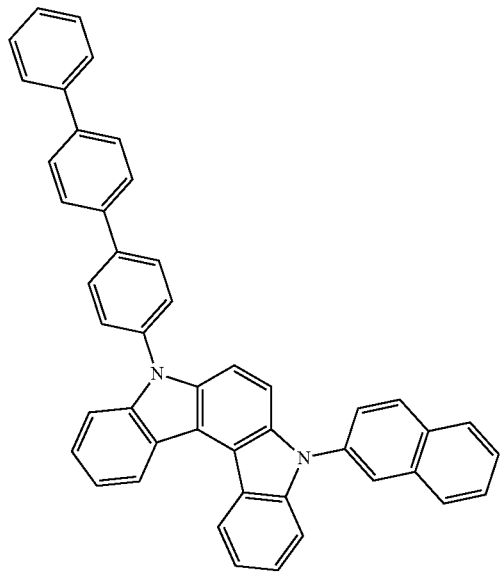
B-84
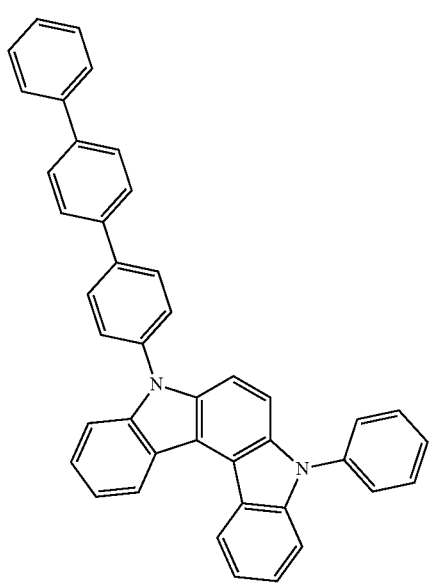
B-85
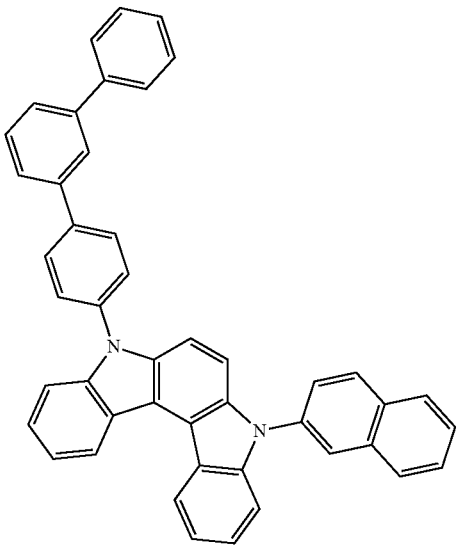
B-86
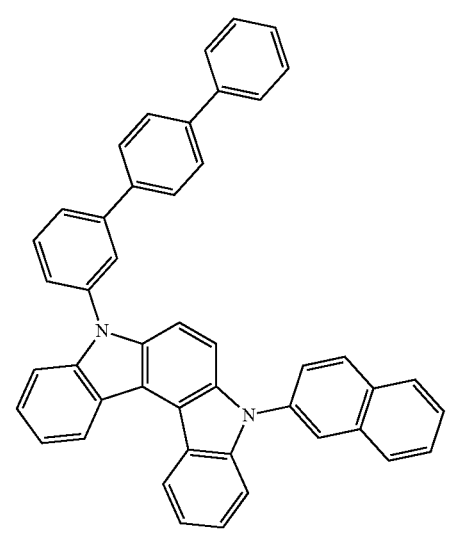
B-87
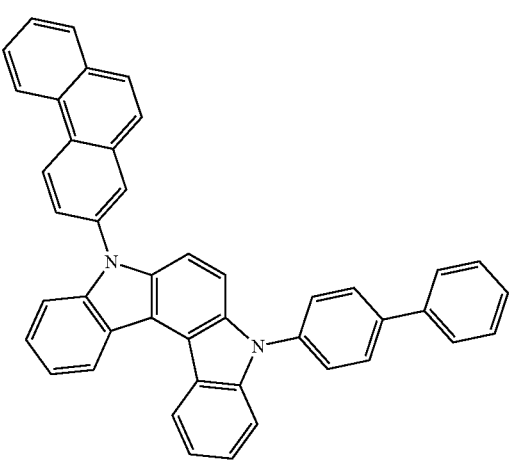

B-88
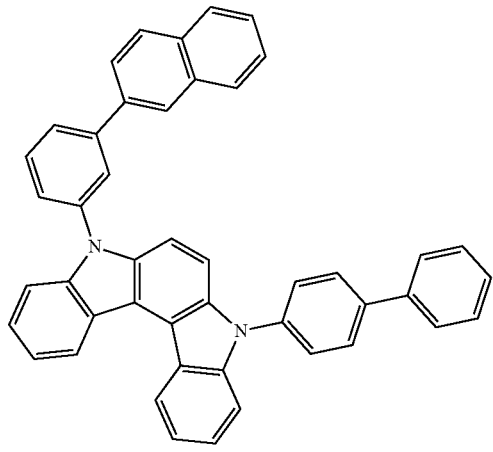
B-91
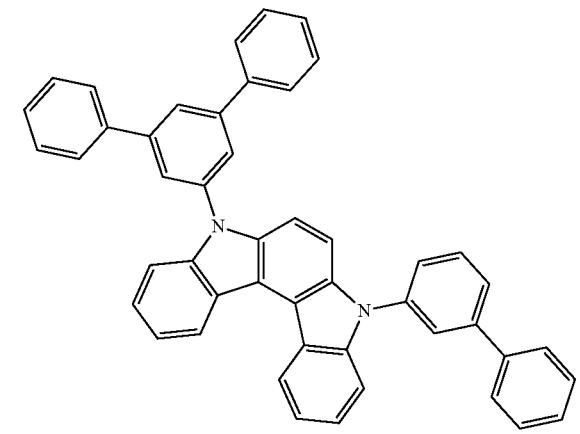
B-89
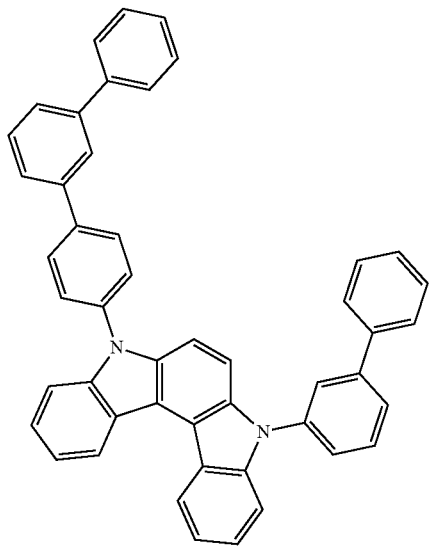
B-92
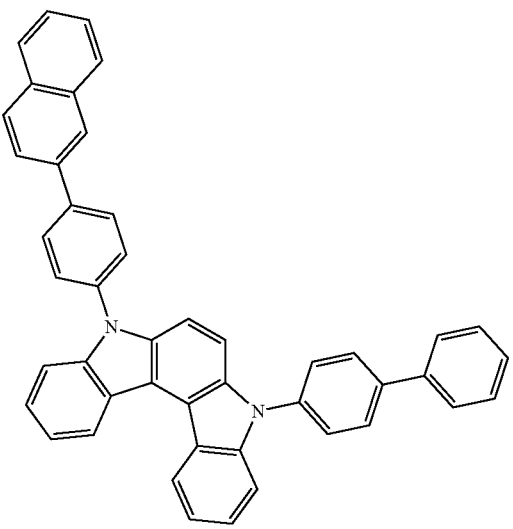
B-90
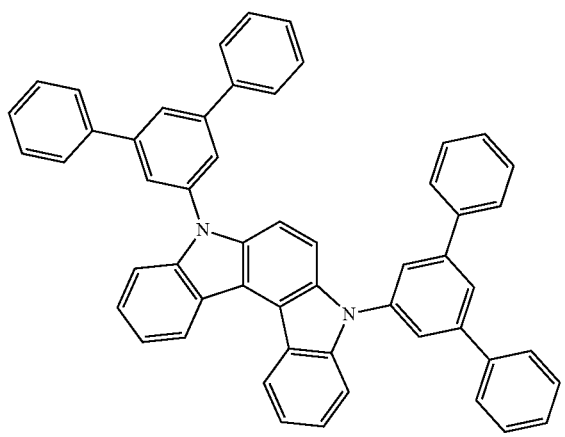
B-93
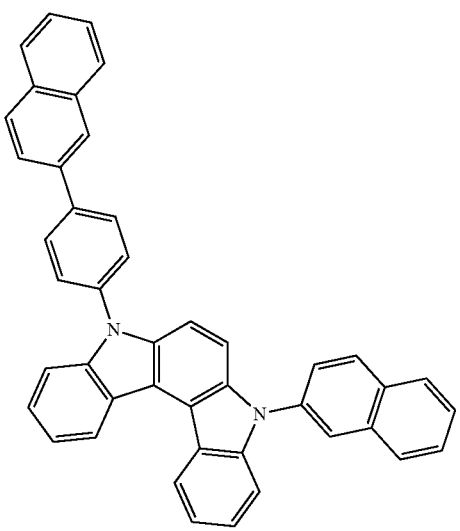

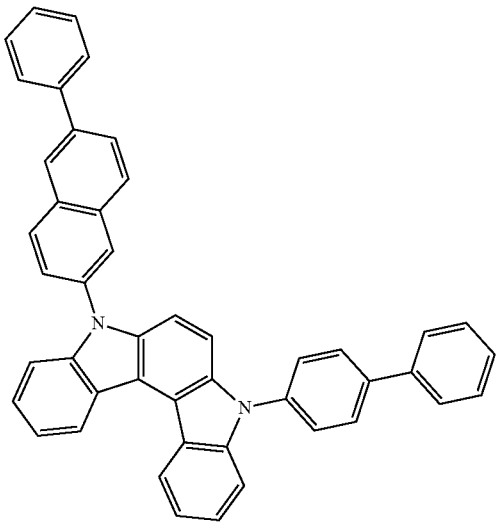

B-94

The first compound for an organic optoelectronic device and the second compound for an organic optoelectronic device may provide various compositions by various combinations.

The second compound for an organic optoelectronic device used with the first compound for an organic optoelectronic device in the light emitting layer and thus increases charge mobility and stability, and thereby a driving voltage, luminous efficiency, and life-span characteristics may be improved. For example, the first compound for an organic optoelectronic device may be represented by Chemical Formula 1A-a or Chemical Formula 1B-a and the second compound for an organic optoelectronic device may be represented by one of Chemical Formula 2A to Chemical Formula 2H.

In more specific examples, the first compound for an organic optoelectronic device may be represented by Chemical Formula 1A-a and the second compound for an organic optoelectronic device may be represented by one of Chemical Formula 2A to Chemical Formula 2H. Herein, L of Chemical Formula 1A-a may be a single bond, a substituted or unsubstituted meta-phenylene group, or a substituted or unsubstituted para-phenylene group, $R^1$ to $R^5$ of Chemical Formula 1A-a may be hydrogen or deuterium, $R^6$ to $R^9$ of Chemical Formula 1A-a may each independently be hydrogen, deuterium, a phenyl group, a biphenyl group, or a naphthyl group or adjacent groups of $R^6$ to $R^9$ may be linked with each other to form a substituted or unsubstituted dibenzofuranyl group, or a substituted or unsubstituted dibenzothiophenyl group, and $Ar^1$ of Chemical Formula 2A to Chemical Formula 2H may be a substituted or unsubstituted phenyl group, or a substituted or unsubstituted biphenyl group, $Ar^2$ of Chemical Formula 2A to Chemical Formula 2H may be a substituted or unsubstituted biphenyl group, a substituted or unsubstituted terphenyl group, or a substituted or unsubstituted triphenylenyl group, $R^{12}$ and $R^{13}$ of Chemical Formula 2A to Chemical Formula 2H may each independently be hydrogen or deuterium, and $R^{10}$, $R^{11}$, $R^{14}$, and $R^{15}$ of Chemical Formula 2A to Chemical Formula 2H may each independently be hydrogen, deuterium, or a phenyl group.

Herein, at least one of $Ar^1$ and the $Ar^2$ may be a substituted or unsubstituted naphthyl group.

In addition, a ratio of the second compound for an organic optoelectronic device and the first compound for an organic optoelectronic device may be adjusted and thereby charge mobility may be controlled. When the composition of the present invention is used as a host, a combination ratio thereof may be different according to types and properties of a used dopant and the first compound for an organic optoelectronic device and the second compound for an organic optoelectronic device may be for example included in a weight ratio of 1:10 to 10:1. Specifically, they may be included in a weight ratio of 2:8 to 8:2, 2:8 to 7:3, 2:8 to 6:4, 3:7 to 8:2, 3:7 to 7:3, and 3:7 to 6:4, for example 3:7 to 6:4. In the most specific examples, a mixing ratio of the first compound for an organic optoelectronic device and the second compound for an organic optoelectronic device may be 3:7, 4:6, 5:5 or 6:4.

Within the ranges, bipolar characteristics may be implemented more effectively, improving efficiency and life-span simultaneously.

The composition may further include at least one host compound in addition the aforementioned first compound for an organic optoelectronic device and second compound for an organic optoelectronic device.

The composition may further include a dopant. The dopant may be a red, green, or blue dopant, for example a red or green phosphorescent dopant.

The dopant is mixed in a small amount to cause light emission, and may be generally a material such as a metal complex that emits light by multiple excitation into a triplet or more. The dopant may be, for example an inorganic, organic, or organic/inorganic compound, and one or more types thereof may be used.

The dopant may be for example a phosphorescent dopant and examples of the phosphorescent dopant may be an organometallic compound including Ir, Pt, Os, Ti, Zr, Hf, Eu, Tb, Tm, Fe, Co, Ni, Ru, Rh, Pd, or a combination thereof. The phosphorescent dopant may be for example a compound represented by Chemical Formula Z, but is not limited thereto.

$$L_2MX \qquad \text{[Chemical Formula Z]}$$

In Chemical Formula Z, M is a metal, and L and X are the same or different, and are a ligand to form a complex compound with M.

The M may be for example Ir, Pt, Os, Ti, Zr, Hf, Eu, Tb, Tm, Fe, Co, Ni, Ru, Rh, Pd, or a combination thereof and the L and X may be for example a bidendate ligand.

The composition may be formed by a dry film formation method such as chemical vapor deposition (CVD) or a solution process.

Hereinafter, an organic optoelectronic device including the aforementioned composition for an organic optoelectronic device is described.

An organic optoelectronic device according to another embodiment includes an anode and a cathode facing each other and at least one organic layer disposed between the anode and the cathode, wherein the organic layer includes the aforementioned composition for an organic optoelectronic device.

For example, the organic layer may include a light emitting layer and the light emitting layer may include the composition for an organic optoelectronic device of the present invention.

Specifically, the composition for an organic optoelectronic device may be included as a host, for example a green host or red host of the light emitting layer.

In addition, the organic layer may include a light emitting layer and at least one auxiliary layer selected from a hole injection layer, a hole transport layer, an electron blocking layer, an electron transport layer, an electron injection layer, and a hole blocking layer and the auxiliary layer may include the composition for an organic optoelectronic device.

The organic optoelectronic device may be any element to convert electrical energy into photoenergy and vice versa without particular limitation, and may be, for example an organic photoelectric element, an organic light emitting diode, an organic solar cell, and an organic photo conductor drum.

Herein, an organic light emitting diode as one example of an organic optoelectronic device is described referring to drawings.

FIGS. 1 and 2 are cross-sectional views of an organic light emitting diode according to embodiments.

Referring to FIG. 1, an organic light emitting diode 100 according to an embodiment includes an anode 120 and a cathode 110 facing each other and an organic layer 105 interposed between the anode 120 and cathode 110.

The anode 120 may be made of a conductor having a large work function to help hole injection, and may be for example a metal, a metal oxide and/or a conductive polymer. The anode 120 may be, for example a metal such as nickel, platinum, vanadium, chromium, copper, zinc, gold, and the like or an alloy thereof; a metal oxide such as zinc oxide, indium oxide, indium tin oxide (ITO), indium zinc oxide (IZO), and the like; a combination of a metal and an oxide such as ZnO and Al or $SnO_2$ and Sb; a conductive polymer such as poly(3-methylthiophene), poly(3,4-(ethylene-1,2-dioxy)thiophene) (PEDOT), polypyrrole, and polyaniline, but is not limited thereto.

The cathode 110 may be made of a conductor having a small work function to help electron injection, and may be for example a metal, a metal oxide, and/or a conductive polymer. The cathode 110 may be for example a metal such as magnesium, calcium, sodium, potassium, titanium, indium, yttrium, lithium, gadolinium, aluminum silver, tin, lead, cesium, barium, and the like or an alloy thereof; a multi-layer structure material such as LiF/Al, $LiO_2$/Al, LiF/Ca, LiF/Al, and $BaF_2$/Ca, but is not limited thereto.

The organic layer 105 includes a light emitting layer 130 including the aforementioned compound for an organic optoelectronic device.

FIG. 2 is a cross-sectional view showing an organic light emitting diode according to another embodiment.

Referring to FIG. 2, an organic light emitting diode 200 further includes a hole auxiliary layer 140 in addition to the light emitting layer 130. The hole auxiliary layer 140 may further increase hole injection and/or hole mobility and block electrons between the anode 120 and the light emitting layer 130. The hole auxiliary layer 140 may be, for example a hole transport layer, a hole injection layer, and/or an electron blocking layer and may include at least one layer.

The organic layer 105 of FIG. 1 or 2 may further include an electron injection layer, an electron transport layer, an electron transport auxiliary layer, a hole transport layer, a hole transport auxiliary layer, a hole injection layer, or a combination thereof even if they are not shown. The compound for an organic optoelectronic device of the present invention may be included in the organic layer. The organic light emitting diodes 100 and 200 may be manufactured by forming an anode or a cathode on a substrate, forming an organic layer using a dry film formation method such as a vacuum deposition method (evaporation), sputtering, plasma plating, and ion plating or a wet coating method such as spin coating, dipping, and flow coating, and forming a cathode or an anode thereon.

The organic light emitting diode may be applied to an organic light emitting diode (OLED) display.

Hereinafter, the embodiments are illustrated in more detail with reference to examples. These examples, however, are not in any sense to be interpreted as limiting the scope of the invention.

Hereinafter, starting materials and reactants used in Examples and Synthesis Examples were purchased from Sigma-Aldrich Co. Ltd. or TCI Inc. as far as there are no particular descriptions or were synthesized by known methods.

(Preparation of Compound for Organic Optoelectronic Device)

The compound as one specific examples of the present invention was synthesized through the following steps.

(First Compound for Organic Optoelectronic Device)

(Synthesis Examples 1 to 6 in the following Table 1 are a known method.)

TABLE 1

| Synthesis Example | Starting material 1 | Starting material 2 |
|---|---|---|
| 1 | | |

TABLE 1-continued
| | | |
|---|---|---|
| 2 | 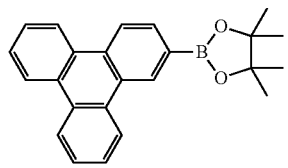 [SMILES: CC1(C)OB(c2ccc3c4ccccc4c4ccccc4c3c2)OC1(C)C] | 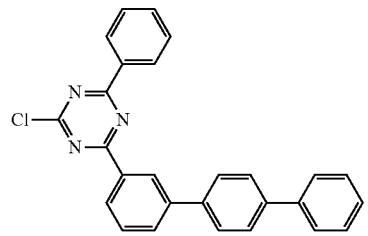 [SMILES: Clc1nc(-c2ccccc2)nc(-c2cccc(-c3ccc(-c4ccccc4)cc3)c2)n1] |
| 3 | 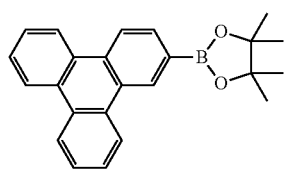 [SMILES: CC1(C)OB(c2ccc3c4ccccc4c4ccccc4c3c2)OC1(C)C] | 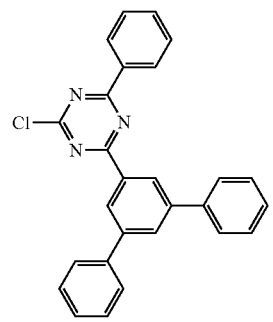 [SMILES: Clc1nc(-c2ccccc2)nc(-c2cc(-c3ccccc3)cc(-c3ccccc3)c2)n1] |
| 4 | 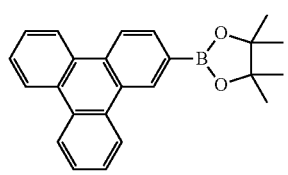 [SMILES: CC1(C)OB(c2ccc3c4ccccc4c4ccccc4c3c2)OC1(C)C] | 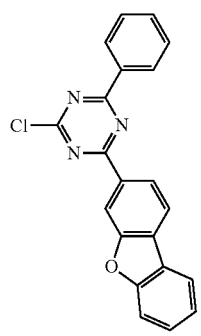 [SMILES: Clc1nc(-c2ccccc2)nc(-c2ccc3c(c2)oc2ccccc23)n1] |
| 5 | 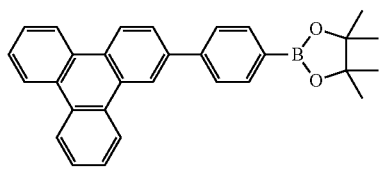 [SMILES: CC1(C)OB(c2ccc(-c3ccc4c5ccccc5c5ccccc5c4c3)cc2)OC1(C)C] | 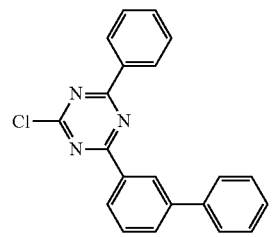 [SMILES: Clc1nc(-c2ccccc2)nc(-c2cccc(-c3ccccc3)c2)n1] |
| 6 | 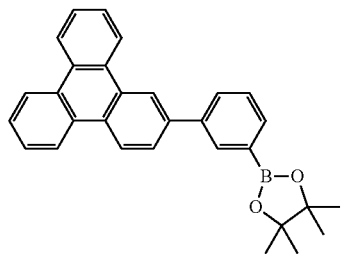 [SMILES: CC1(C)OB(c2cccc(-c3ccc4c5ccccc5c5ccccc5c4c3)c2)OC1(C)C] | 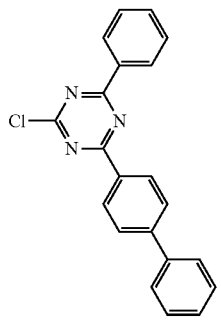 [SMILES: Clc1nc(-c2ccccc2)nc(-c2ccc(-c3ccccc3)cc2)n1] |

TABLE 1-continued
| Synthesis Example | Product | Yield (%) |
|---|---|---|
| 1 | 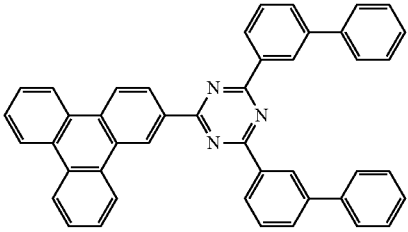<br>A-31 | 78% |
| 2 | 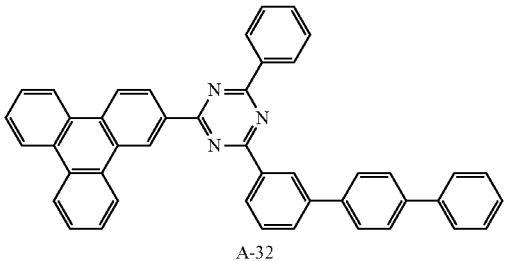<br>A-32 | 80% |
| 3 | 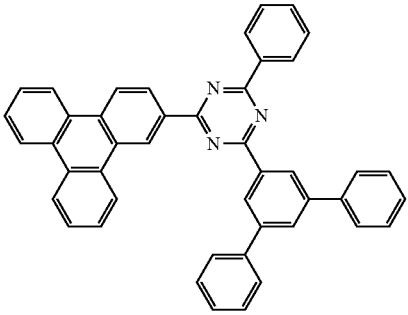<br>A-36 | 83% |
| 4 | 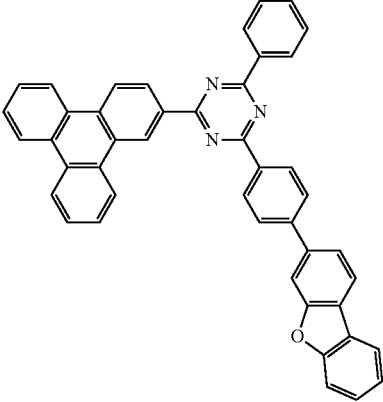<br>A-37 | 85% |

TABLE 1-continued

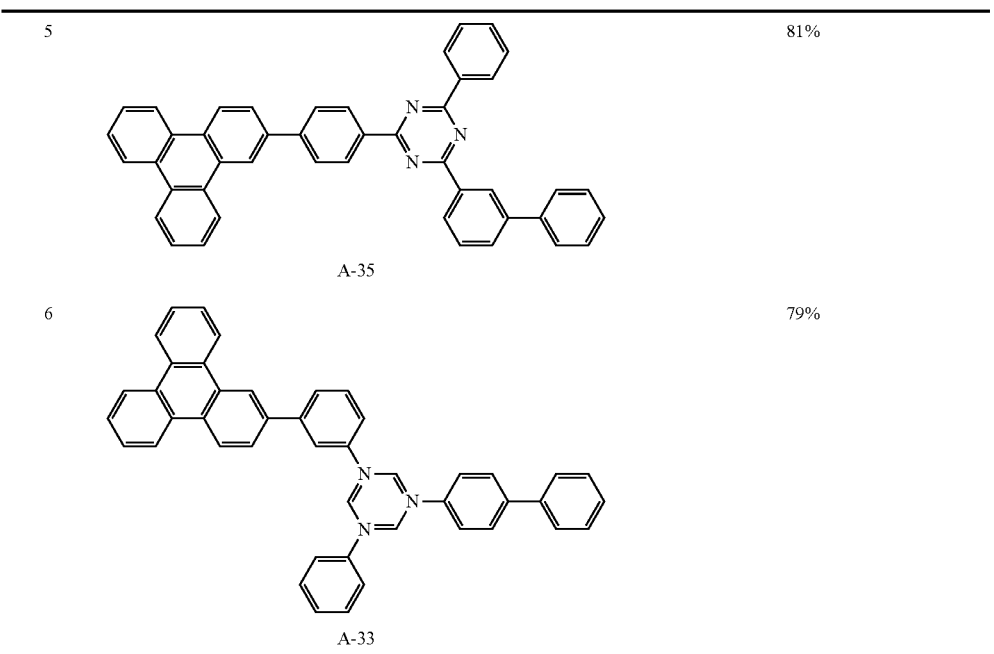

The first compound for an organic optoelectronic device was prepared according to a similar method thereto.
(Second Compound for Organic Optoelectronic Device)

Synthesis Example 7 Synthesis of Compound B-9

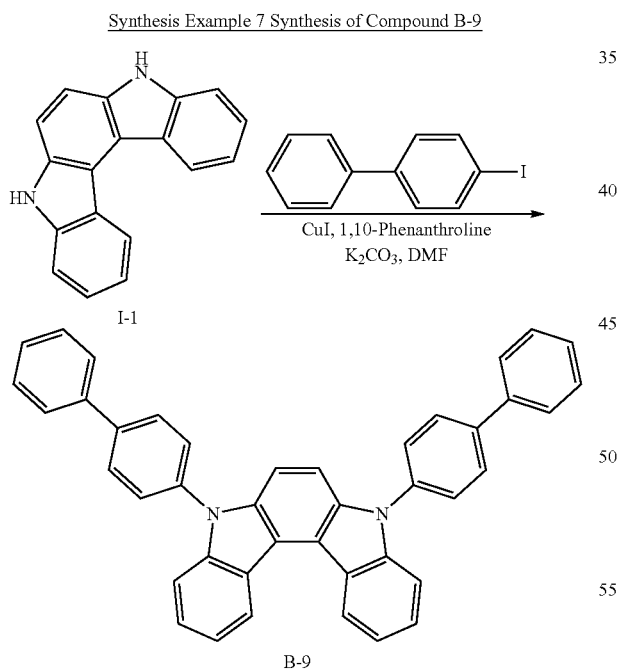

8 g (31.2 mmol) of Intermediate I-1, 20.5 g (73.32 mmol) of 4-iodobiphenyl, 1.19 g (6.24 mmol) of CuI, 1.12 g (6.24 mmol) of 1,10-phenanthroline, and 12.9 g (93.6 mmol) of $K_2CO_3$ were put in a round-bottomed flask, 50 ml of DMF was added thereto to dissolve them, and the solution was refluxed and stirred under a nitrogen atmosphere for 24 hours. When a reaction was complete, distilled water was added thereto, and a precipitate therefrom was filtered. The solid was dissolved in 250 ml of xylene, filtered with silica gel, and precipitated into a white solid to obtain 16.2 g of a target compound, B-9 (yield: 93%).

Compound B-20, Compound B-43, and Compound B-84 were synthesized in the same manner as Synthesis Example 7 by using 3-iodobiphenyl and bromotriphenylene, which are known intermediates instead of the reactant, 4-iodobiphenyl of Synthesis Example 7.

On the other hand, the second compound for an organic optoelectronic device of the present invention was synthesized using or another known indolocarbazole moiety as a starting material, instead of the starting material 1-1 of Synthesis Example 7.
(Manufacture of Organic Light Emitting Diode)

Example 1: Green Light Emitting Diode

A glass substrate coated with ITO (indium tin oxide) as a 1500 Å-thick thin film was ultrasonic wave-washed with distilled water. After washing with the distilled water, the glass substrate was ultrasonic wave-washed with a solvent such as isopropyl alcohol, acetone, methanol, and the like and dried and then, moved to a plasma cleaner, cleaned by using oxygen plasma for 10 minutes, and moved to a vacuum depositor. This obtained ITO transparent electrode was used as an anode, a 700 Å-thick hole injection layer was formed on the ITO substrate by vacuum depositing Compound A, and a hole transport layer was formed on the injection layer by depositing Compound B to be 50 Å thick and Compound C to be 1020 Å thick. On the hole transport layer, a 400 Å-thick light emitting layer was formed by simultaneously vacuum-depositing Compound A-31 and Compound B-43 as a host and being doped with 10 wt % of tris(2-phenylpyridine)iridium(III) [Ir(ppy)$_3$] or PhGD as a dopant. Herein, Compound A-31 and Compound B-43 were used in a ratio of 3:7 and the ratios were separately in the following examples. Subsequently, Compound D and Liq were vacuum-deposited simultaneously at a 1:1 ratio on the light emitting layer to form a 300 Å-thick electron transport layer and a cathode was formed by sequentially vacuum-depositing Liq to be 15 Å thick and Al to be 1200 Å thick on the electron transport layer, manufacturing an organic light emitting diode.

The organic light emitting diode had a five-layered organic thin layer structure as follows:

A structure of ITO/Compound A (700 Å)/Compound B (50 Å)/Compound C (1020 Å)/EML [Compound A-31: B-43: Ir(ppy)$_3$ or PhGD=27 wt %:63 wt %:10 wt %] (400 Å)/Compound D: Liq (300 Å)/Liq (15 Å)/Al (1200 Å).

Compound A: N4,N4'-diphenyl-N4,N4'-bis(9-phenyl-9H-carbazol-3-yl)biphenyl-4,4'-diamine Compound B: 1,4,5,8,9,11-hexaazatriphenylene-hexacarbonitrile (HAT-CN), Compound C: N-(biphenyl-4-yl)-9,9-dimethyl-N-(4-(9-phenyl-9H-carbazol-3-yl)phenyl)-9H-fluoren-2-amine Compound D: 8-(4-(4,6-di(naphthalen-2-yl)-1,3,5-triazin-2-yl)phenyl)quinoline Examples 2 to 20, Examples 41 to 52 and Comparative Examples 1 and 2

Diodes of Examples 2 to 20, Examples 41 to 52, and Comparative Examples 1 and 2 were manufactured in the same manner as Example 1 using the first hosts and the second hosts, respectively, as shown in Table 2 and Table 4.

Example 21: Red Light Emitting Diode

A glass substrate coated with ITO (indium tin oxide) as a 1500 Å-thick thin film was washed with distilled water. After washing with the distilled water, the glass substrate was ultrasonic wave-washed with a solvent such as isopropyl alcohol, acetone, methanol, and the like and dried and then, moved to a plasma cleaner, cleaned by using oxygen plasma for 10 minutes, and moved to a vacuum depositor. This obtained ITO transparent electrode was used as an anode, Compound A was vacuum-deposited on the ITO substrate to form a 700 Å-thick hole injection layer, Compound B was deposited to be 50 Å thick on the injection layer, and Compound C was deposited to be 700 Å thick to form a hole transport layer. On the hole transport layer, a 400 Å-thick hole transport auxiliary layer was formed by vacuum-depositing Compound C-1. On the hole transport auxiliary layer, a 400 Å-thick light emitting layer was formed by vacuum-depositing Compound A-35 and Compound B-9 simultaneously as a host and doping 2 wt % of [Ir(piq)$_2$acac] as a dopant. Herein, Compound A-35 and Compound B-9 were used in a weight ratio of 1:1, and their weight ratios are separately in the following examples. Subsequently, on the light emitting layer, a 300 Å-thick electron transport layer was formed by simultaneously vacuum-depositing Compound D and Liq in a ratio of 1:1, and on the electron transport layer, Liq and Al were sequentially vacuum-deposited to be 15 Å thick and 1200 Å thick, manufacturing an organic light emitting diode.

The organic light emitting diode included a five-layered organic thin layer, and specifically the following structure.

ITO/Compound A (700 Å)/Compound B (50 Å)/Compound C (700 Å)/Compound C-1 (400 Å)/EML [Compound A-35: B-9: [Ir(piq)$_2$acac] (2 wt %)] (400 Å)/Compound D: Liq (300 Å)/Liq (15 Å)/Al (1200 Å).

Compound C-1: N,N-di([1,1'-biphenyl]-4-yl)-7,7-dimethyl-7H-fluoreno[4,3-b]benzofuran-10-amine Examples 22 to 40, Examples 53 and 63 and Comparative Example 3

The diodes of Example 22 to 40, Example 53 to 63 and Comparative Example 3 were manufactured in the same manner as Example 21 using the first hosts and the second hosts, respectively, as shown in Table 3 and Table 5.

Evaluation

The following effects of organic light emitting diodes according to Example 1 to 63 and Comparative Example 1 to 3 were evaluated.

Specific measurement methods are as follows, and the results are shown in Tables 2 to 5.

(1) Measurement of Driving Voltage

A driving voltage of each diode was measured using a current-voltage meter (Keithley 2400) at 15 mA/cm$^2$.

TABLE 2

| | | | Green diode | | | |
|---|---|---|---|---|---|---|
| Example | First host | Second host | First host: second host (wt/wt) | Dopant | Color | Driving voltage (V) |
| Example 1 | A-31 | B-43 | 3:7 | Ir(ppy)$_3$ | green | 4.04 |
| Example 2 | A-31 | B-43 | 5:5 | Ir(ppy)$_3$ | green | 3.84 |
| Example 3 | A-31 | B-45 | 3:7 | Ir(ppy)$_3$ | green | 4.04 |
| Example 4 | A-31 | B-45 | 4:6 | Ir(ppy)$_3$ | green | 3.80 |
| Example 5 | A-8 | B-9 | 3:7 | PhGD | green | 4.25 |
| Example 6 | A-8 | B-9 | 4:6 | PhGD | green | 4.22 |
| Example 7 | A-8 | B-9 | 5:5 | PhGD | green | 4.12 |
| Example 8 | A-8 | B-9 | 6:4 | PhGD | green | 4.14 |
| Example 9 | A-32 | B-9 | 3:7 | PhGD | green | 4.13 |
| Example 10 | A-32 | B-9 | 5:5 | PhGD | green | 4.04 |
| Example 11 | A-33 | B-9 | 4:6 | PhGD | green | 4.02 |
| Example 12 | A-33 | B-9 | 5:5 | PhGD | green | 4.00 |
| Example 13 | A-33 | B-9 | 6:4 | PhGD | green | 3.98 |
| Example 14 | A-8 | B-84 | 6:4 | PhGD | green | 4.20 |
| Example 15 | A-8 | B-82 | 4:6 | PhGD | green | 4.29 |
| Example 16 | A-8 | B-82 | 5:5 | PhGD | green | 4.22 |
| Example 17 | A-8 | B-83 | 5:5 | PhGD | green | 4.22 |
| Example 18 | A-8 | B-87 | 4:6 | PhGD | green | 4.16 |
| Example 19 | A-8 | B-87 | 5:5 | PhGD | green | 4.19 |
| Example 20 | A-54 | B-9 | 5:5 | PhGD | green | 4.07 |
| Comparative Example 1 | A-8 | R-1 | 3:7 | Ir(ppy)$_3$ | green | 4.39 |
| Comparative Example 2 | A-8 | R-1 | 3:7 | PhGD | green | 4.80 |

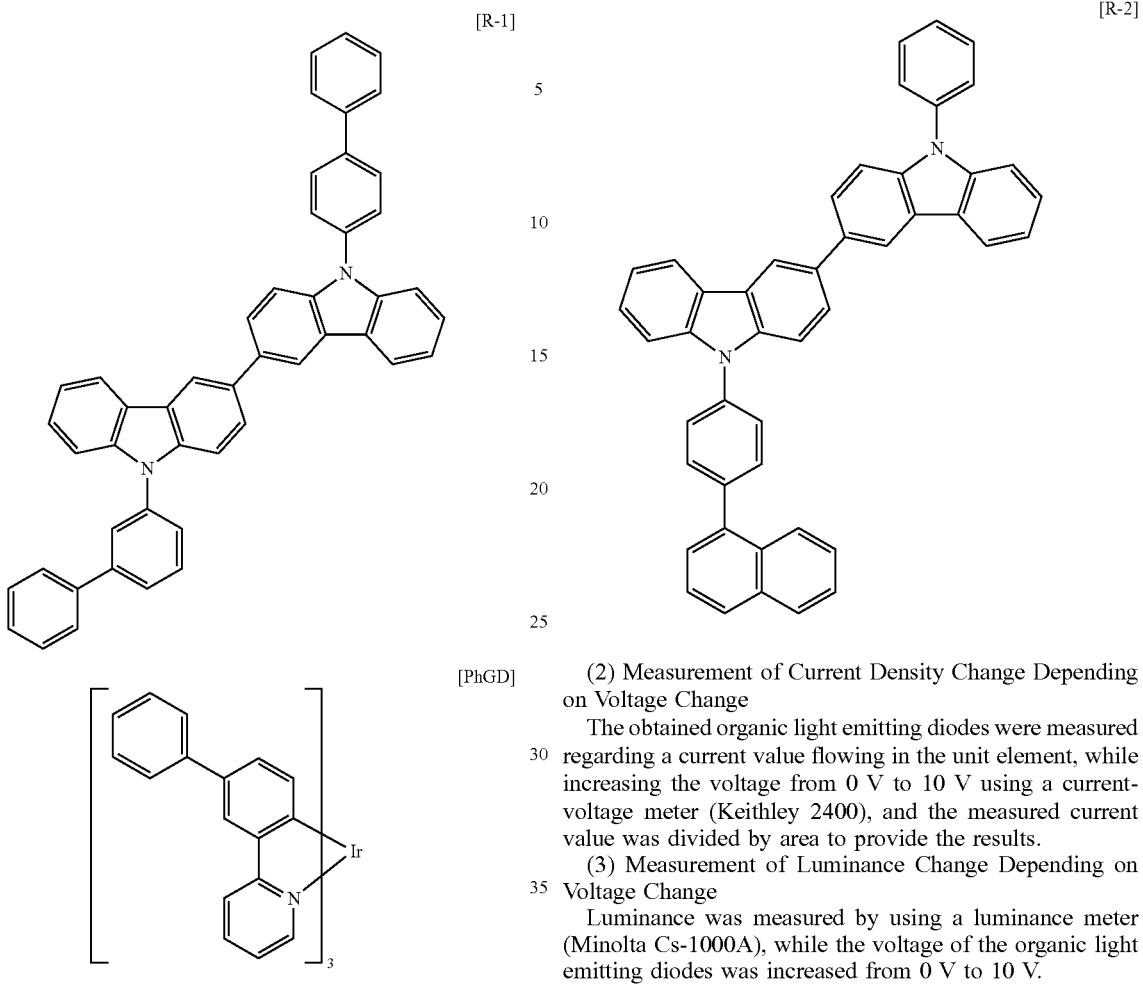

(2) Measurement of Current Density Change Depending on Voltage Change

The obtained organic light emitting diodes were measured regarding a current value flowing in the unit element, while increasing the voltage from 0 V to 10 V using a current-voltage meter (Keithley 2400), and the measured current value was divided by area to provide the results.

(3) Measurement of Luminance Change Depending on Voltage Change

Luminance was measured by using a luminance meter (Minolta Cs-1000A), while the voltage of the organic light emitting diodes was increased from 0 V to 10 V.

(4) Measurement of Luminous Efficiency

Current efficiency (cd/A) at the same current density (10 mA/cm$^2$) were calculated by using the luminance, current density, and voltages (V) from the items (2) and (3).

(5) Measurement of Life-Span

T90 life-spans of the organic light emitting diodes (green diodes) according to Examples 41 to 53 were measured as a time when their luminance decreased down to 90% relative to the initial luminance after emitting light with 24000 cd/m$^2$ as the initial luminance (cd/m$^2$) and measuring their luminance decrease depending on a time with a Polanonix life-span measurement system. T97 life-spans of the organic light emitting diodes (red diodes) according to Examples 54 and 64 were measured as a time when their luminance decreased down to 97% relative to the initial luminance after emitting light with 6000 cd/m$^2$ as the initial luminance (cd/m$^2$)

TABLE 3

Red diode

| Example | First host | Second host | First host:second host (wt/wt) | Dopant | Color | Driving voltage (V) |
|---|---|---|---|---|---|---|
| Example 21 | A-35 | B-9 | 3:7 | Ir(piq)$_2$acac | red | 3.85 |
| Example 22 | A-35 | B-20 | 3:7 | Ir(piq)$_2$acac | red | 4.10 |
| Example 23 | A-36 | B-9 | 3:7 | Ir(piq)$_2$acac | red | 4.09 |
| Example 24 | A-36 | B-9 | 5:5 | Ir(piq)$_2$acac | red | 3.80 |
| Example 25 | A-35 | B-11 | 5:5 | Ir(piq)$_2$acac | red | 3.95 |
| Example 26 | A-35 | B-22 | 5:5 | Ir(piq)$_2$acac | red | 3.97 |
| Example 27 | A-35 | B-84 | 3:7 | Ir(piq)$_2$acac | red | 3.89 |
| Example 28 | A-35 | B-84 | 5:5 | Ir(piq)$_2$acac | red | 3.62 |
| Example 29 | A-35 | B-83 | 3:7 | Ir(piq)$_2$acac | red | 3.88 |
| Example 30 | A-35 | B-85 | 3:7 | Ir(piq)$_2$acac | red | 4.01 |
| Example 31 | A-53 | B-83 | 3:7 | Ir(piq)$_2$acac | red | 4.11 |
| Example 32 | A-35 | B-14 | 3:7 | Ir(piq)$_2$acac | red | 4.15 |
| Example 33 | A-35 | B-87 | 3:7 | Ir(piq)$_2$acac | red | 3.92 |
| Example 34 | A-32 | B-83 | 3:7 | Ir(piq)$_2$acac | red | 4.03 |
| Example 35 | A-36 | B-83 | 3:7 | Ir(piq)$_2$acac | red | 4.06 |
| Example 36 | A-33 | B-83 | 3:7 | Ir(piq)$_2$acac | red | 3.96 |
| Example 37 | A-35 | B-92 | 3:7 | Ir(piq)$_2$acac | red | 3.82 |
| Example 38 | A-35 | B-93 | 3:7 | Ir(piq)$_2$acac | red | 3.75 |
| Example 39 | A-55 | B-83 | 3:7 | Ir(piq)$_2$acac | red | 4.07 |
| Example 40 | A-55 | B-92 | 3:7 | Ir(piq)$_2$acac | red | 4.02 |
| Comparative Example 3 | A-35 | R-2 | 3:7 | Ir(piq)$_2$acac | red | 4.53 |

TABLE 4

Green diode

| Example | First host | Second host | First host:second host (wt/wt) | Color | Life-span (T90) | Light emitting efficiency (cd/A) |
|---|---|---|---|---|---|---|
| Example 41 | A-8 | B-9 | 4:6 | green | 110 | 71.5 |
| Example 42 | A-8 | B-9 | 3:7 | green | 83 | 69.8 |
| Example 43 | A-33 | B-9 | 4:6 | green | 110 | 70.0 |

TABLE 4-continued

Green diode

| Example | First host | Second host | First host: second host (wt/wt) | Color | Life-span (T90) | Light emitting efficiency (cd/A) |
|---|---|---|---|---|---|---|
| Example 44 | A-32 | B-9 | 5:5 | green | 88 | 69.0 |
| Example 45 | A-8 | B-11 | 3:7 | green | 80 | 68.8 |
| Example 46 | A-8 | B-9 | 5:5 | green | 150 | 72.9 |
| Example 47 | A-8 | B-82 | 4:6 | green | 77 | 73.9 |
| Example 48 | A-8 | B-82 | 5:5 | green | 180 | 72.8 |
| Example 49 | A-8 | B-85 | 5:5 | green | 125 | 68.5 |
| Example 50 | A-8 | B-14 | 5:5 | green | 150 | 68.1 |
| Example 51 | A-8 | B-90 | 5:5 | green | 160 | 66.0 |
| Example 52 | A-8 | B-91 | 5:5 | green | 145 | 69.0 |

TABLE 5

Red diode

| Example | First host | Second host | First host: second host (wt/wt) | Color | Life-span (T97) | Light emitting efficiency (cd/A) |
|---|---|---|---|---|---|---|
| Example 53 | A-35 | B-9 | 3:7 | red | 132 | 20.8 |
| Example 54 | A-35 | B-20 | 3:7 | red | 70 | 20.8 |
| Example 55 | A-35 | B-84 | 3:7 | red | 84 | 22.3 |
| Example 56 | A-35 | B-83 | 3:7 | red | 235 | 22.9 |
| Example 57 | A-32 | B-83 | 3:7 | red | 195 | 21.9 |
| Example 58 | A-33 | B-83 | 3:7 | red | 193 | 21.3 |
| Example 59 | A-35 | B-92 | 3:7 | red | 190 | 22.6 |
| Example 60 | A-35 | B-93 | 3:7 | red | 188 | 21.9 |
| Example 61 | A-54 | B-83 | 3:7 | red | 175 | 21.6 |
| Example 62 | A-55 | B-83 | 3:7 | red | 148 | 21.8 |
| Example 63 | A-55 | B-92 | 3:7 | red | 132 | 21.9 |

Referring to Tables 2 and 3, the driving voltages of the organic light emitting diodes using combinations of the first hosts and the second hosts were lower than those of the comparative examples.

Referring to Tables 4 and 5, the compositions of the present invention exhibited excellent life-span and luminous efficiency.

While this invention has been described in connection with what is presently considered to be practical example embodiments, it is to be understood that the invention is not limited to the disclosed embodiments. On the contrary, it is intended to cover various modifications and equivalent arrangements included within the spirit and scope of the appended claims. Therefore, the aforementioned embodiments should be understood to be exemplary but not limiting the present invention in any way.

DESCRIPTION OF SYMBOLS

100, 200: organic light emitting diode
105: organic layer
110: cathode
120: positive electrode
130: light emitting layer
140: hole auxiliary layer

The invention claimed is:

1. A composition for an organic optoelectronic device, the composition comprising:
a first compound for an organic optoelectronic device represented by Chemical Formula 1; and
a second compound for an organic optoelectronic device, the second compound being represented by a combination of Chemical Formula 2 and Chemical Formula 3A or a combination of Chemical Formula 2 and Chemical Formula 3B:

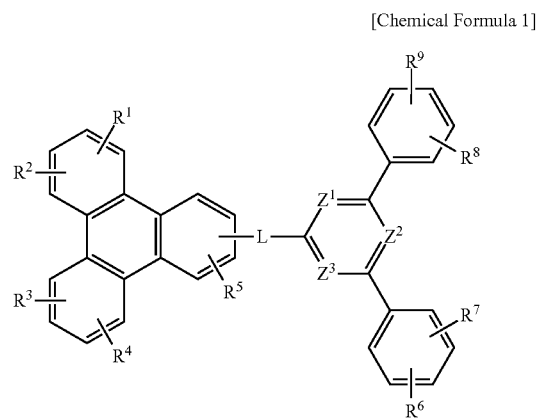

[Chemical Formula 1]

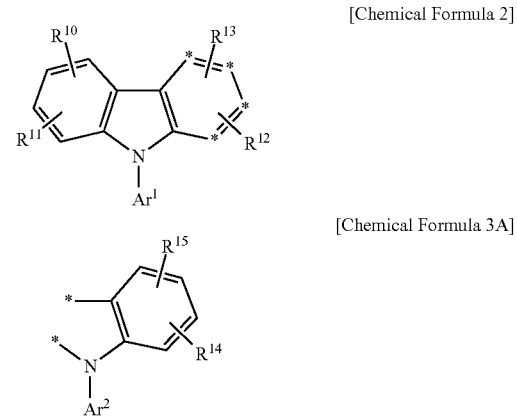

[Chemical Formula 2]

[Chemical Formula 3A]

[Chemical Formula 3B]

wherein, in Chemical Formula 1,
$Z^1$ to $Z^3$ are each independently N or $CR^a$,
at least two of $Z^1$ to $Z^3$ are N,
L is a single bond, or a substituted or unsubstituted C6 to C18 arylene group,
$R^a$ and $R^1$ to $R^9$ are each independently hydrogen, deuterium, a hydroxyl group, a thiol group, a cyano group, a substituted or unsubstituted C1 to C20 alkyl group, or a substituted or unsubstituted C6 to C18 aryl group, and
$R^6$ to $R^9$ are each independently present or adjacent groups thereof are linked with each other to form a substituted or unsubstituted dibenzofuranyl group, or a substituted or unsubstituted dibenzothiophenyl group;
wherein, in Chemical Formula 2, Chemical Formula 3A, and Chemical Formula 3B,
$Ar^1$ is a substituted or unsubstituted phenyl group, a substituted or unsubstituted biphenyl group, or a substituted or unsubstituted naphthyl group,
$Ar^2$ is a substituted or unsubstituted biphenyl group, a substituted or unsubstituted terphenyl group, a substituted or unsubstituted naphthyl group, a substituted or unsubstituted anthracenyl group, a substituted or unsubstituted phenanthrenyl group, or a substituted or unsubstituted triphenylenyl group, adjacent two "*" of Chemical Formula 2 are linked with "*" of Chemical Formula 3A or adjacent two "*" of Chemical Formula 3B and remaining "*" of Chemical Formula 2 not linked with Chemical Formula 3A and Chemical Formula 3B and remaining "*" of Chemical Formula 3B not linked with Chemical Formula 2 are C or $CR^b$, $R^b$ and $R^{10}$ to $R^{15}$ are each independently hydrogen, deuterium, a substituted or unsubstituted C1 to C20 alkyl group, or a substituted or unsubstituted C6 to C18 aryl group, and $R^b$ and $R^{10}$ to $R^{15}$ are each independently present or adjacent groups thereof are linked with each other to form a substituted or unsubstituted aliphatic monocyclic ring, aliphatic polycyclic ring, aromatic monocyclic ring, aromatic polycyclic ring, heteroaromatic monocyclic ring or heteroaromatic polycyclic ring.

2. The composition for an organic optoelectronic device of claim 1, wherein Chemical Formula 1 is represented by Chemical Formula 1A or Chemical Formula 1B:

[Chemical Formula 1A]

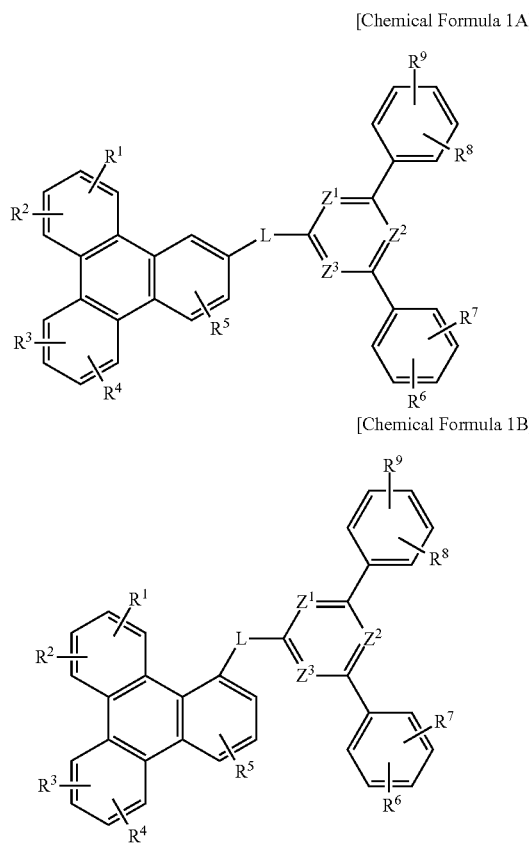

[Chemical Formula 1B]

wherein, in Chemical Formulae 1A and 1B,
$Z^1$ to $Z^3$ are each independently N or $CR^a$,
at least two of $Z^1$ to $Z^3$ are N,
L is a single bond, or a substituted or unsubstituted C6 to C18 arylene group
$R^a$ and $R^1$ to $R^9$ are each independently hydrogen, deuterium, a hydroxyl group, a thiol group, a substituted or unsubstituted C1 to C20 alkyl group, or a substituted or unsubstituted C6 to C18 aryl group, and $R^6$ to $R^9$ are each independently present or adjacent groups thereof are linked with each other to form a substituted or unsubstituted dibenzofuranyl group, or a substituted or unsubstituted dibenzothiophenyl group.

3. The composition for an organic optoelectronic device of claim 1, wherein L is a single bond or one of substituted or unsubstituted linking groups of Group I:

[Group I]

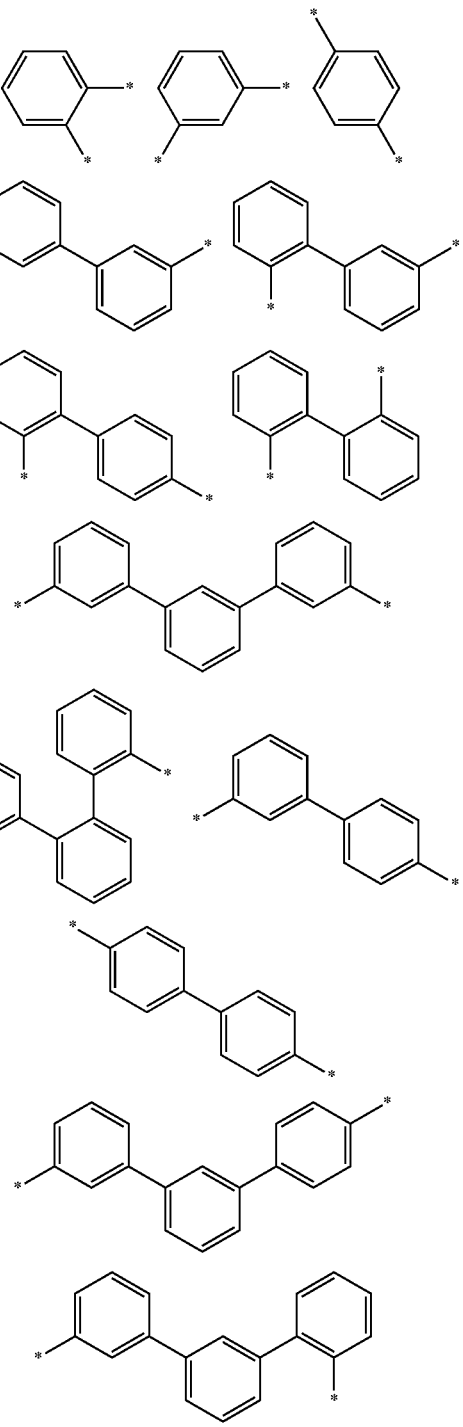

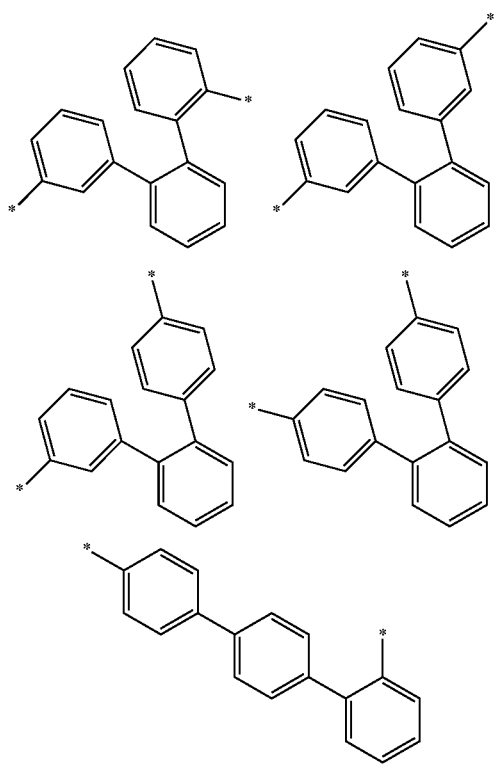
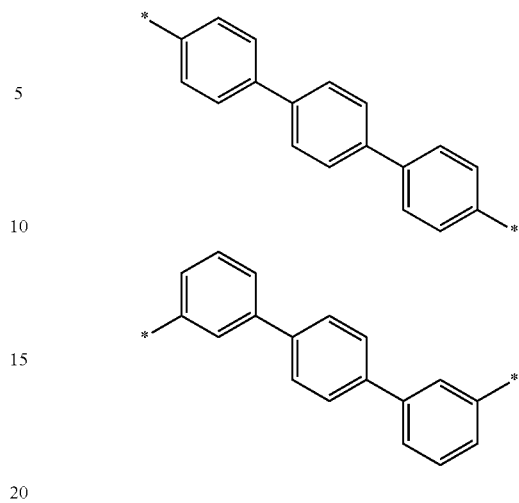
wherein, in Group I, * is a linking point.
4. The composition for an organic optoelectronic device of claim 2, wherein:
Chemical Formula 1 is represented by Chemical Formula 1A, and
Chemical Formula 1A is represented by one of Chemical Formula 1A-1, Chemical Formula 1A-2, Chemical Formula 1A-3, Chemical Formula 1A-4, and Chemical Formula 1A-5:
[Chemical Formula 1A-1]
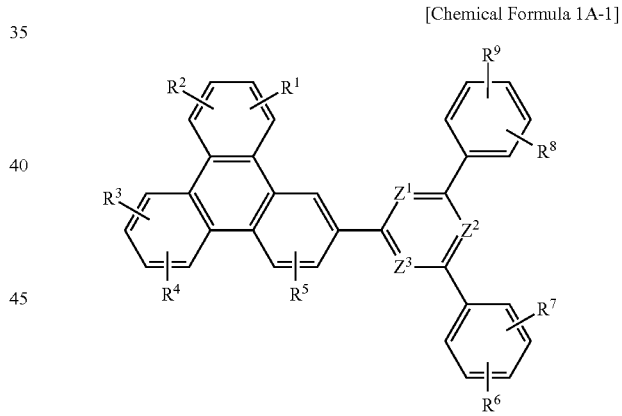
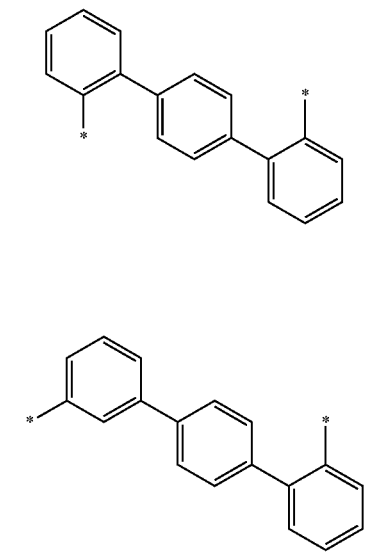
[Chemical Formula 1A-2]
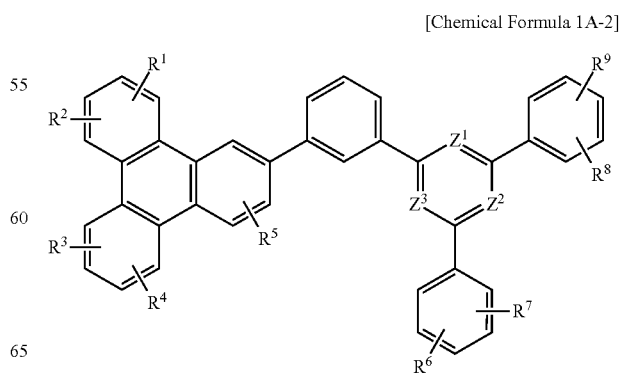

-continued

[Chemical Formula 1A-3]

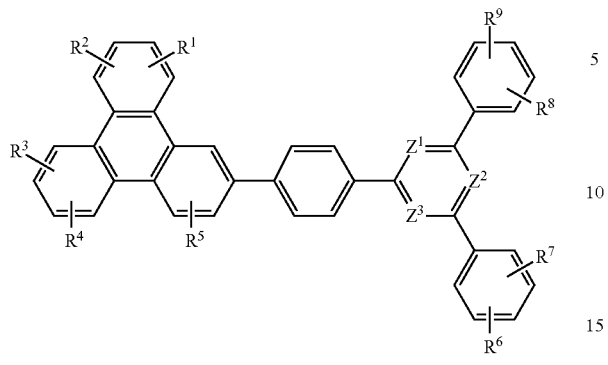

[Chemical Formula 1A-4]

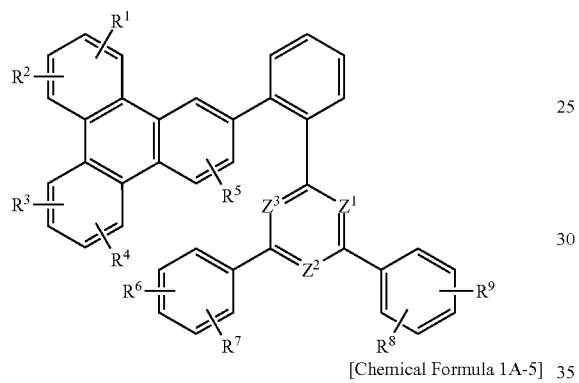

[Chemical Formula 1A-5]

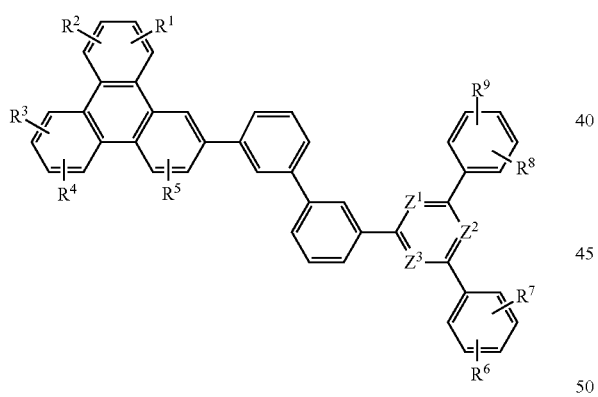

wherein, in Chemical Formulae 1A-1 to 1A-5, $Z^1$ to $Z^3$ are each independently N or $CR^a$, at least two of $Z^1$ to $Z^3$ are N, $R^a$ and $R^1$ to $R^9$ are each independently hydrogen, deuterium, a hydroxyl group, a thiol group, a substituted or unsubstituted C1 to C20 alkyl group, or a substituted or unsubstituted C6 to C18 aryl group, and $R^6$ to $R^9$ are each independently present or adjacent groups thereof are linked with each other to form a substituted or unsubstituted dibenzofuranyl group, or a substituted or unsubstituted dibenzothiophenyl group.

5. The composition for an organic optoelectronic device of claim 1, wherein the second compound is represented by Chemical Formula 2A, Chemical Formula 2B, Chemical Formula 2C, Chemical Formula 2D, Chemical Formula 2E, Chemical Formula 2F, Chemical Formula 2G, or Chemical Formula 2H:

[Chemical Formula 2A]

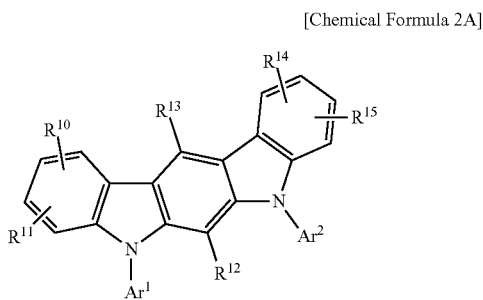

[Chemical Formula 2B]

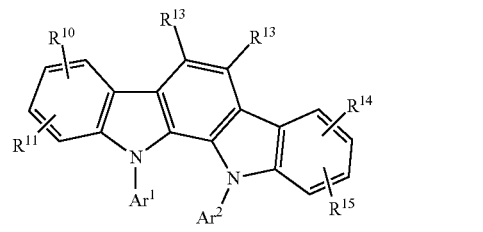

[Chemical Formula 2C]

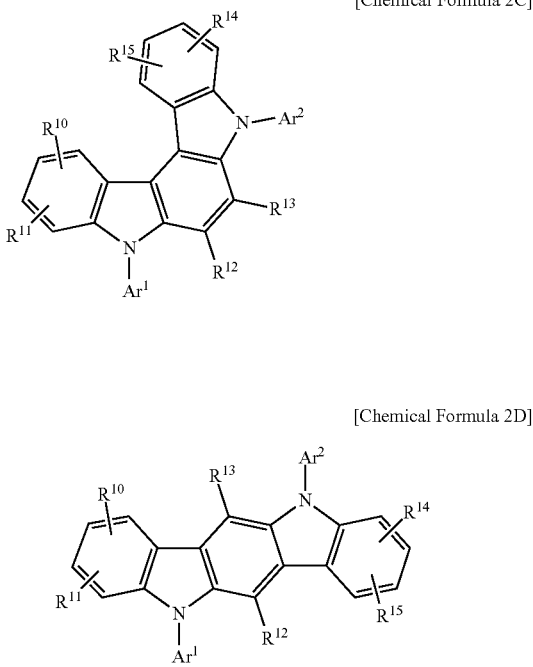

[Chemical Formula 2D]

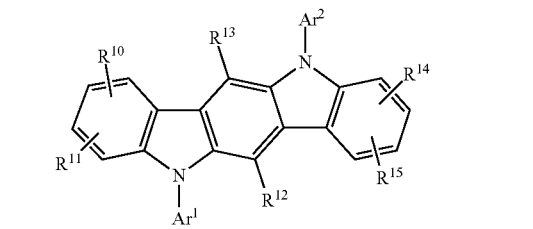

[Chemical Formula 2E]

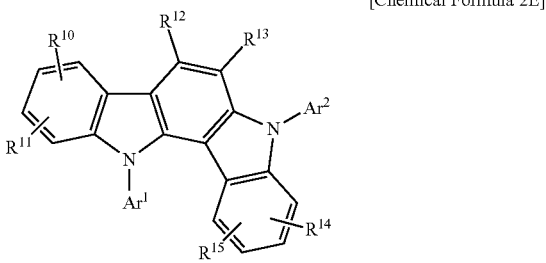

[Chemical Formula 2F]

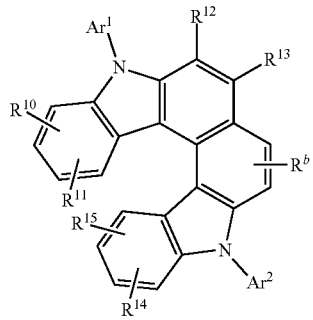

[Chemical Formula 2G]

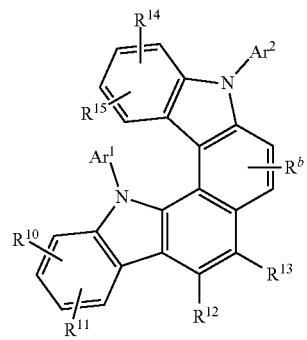

[Chemical Formula 2H]

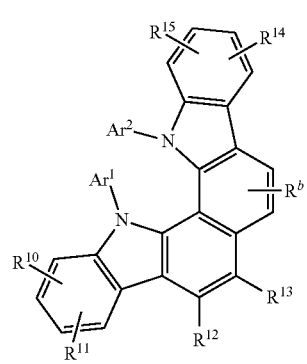

wherein, in Chemical Formula 2A to Chemical Formula 2H,

Ar¹ is a substituted or unsubstituted phenyl group, a substituted or unsubstituted biphenyl group, or a substituted or unsubstituted naphthyl group, Ar² is a substituted or unsubstituted biphenyl group, a substituted or unsubstituted terphenyl group, a substituted or unsubstituted naphthyl group, a substituted or unsubstituted anthracenyl group, a substituted or unsubstituted phenanthrenyl group, or a substituted or unsubstituted triphenylenyl group, and $R^{10}$ to $R^{15}$ are each independently hydrogen, deuterium, a substituted or unsubstituted C1 to C20 alkyl group, or a substituted or unsubstituted C6 to C18 aryl group.

6. The composition for an organic optoelectronic device of claim 1, wherein at least one of Ar¹ and the Ar² is a substituted or unsubstituted naphthyl group.

7. The composition for an organic optoelectronic device of claim 1, wherein:

the first compound for an organic optoelectronic device is represented by Chemical Formula 1A-a, and the second compound for an organic optoelectronic device is represented by Chemical Formula 2A, Chemical Formula 2B, Chemical Formula 2C, Chemical Formula 2D, Chemical Formula 2E, Chemical Formula 2F, Chemical Formula 2G, or Chemical Formula 2H:

[Chemical Formula 1A-a]

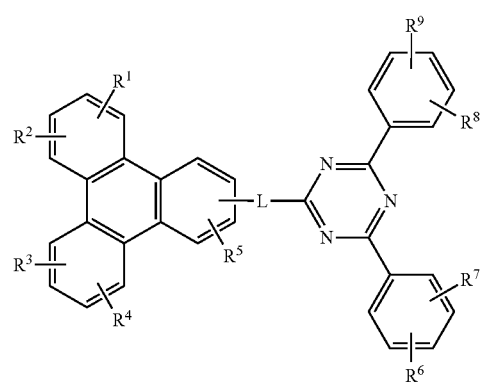

[Chemical Formula 2A]

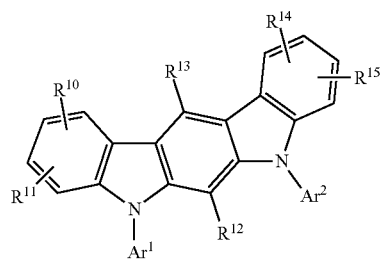

[Chemical Formula 2B]

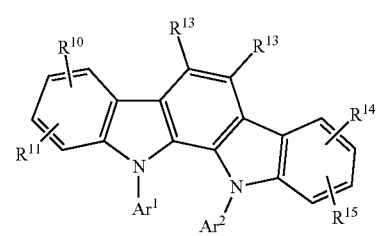

[Chemical Formula 2C]

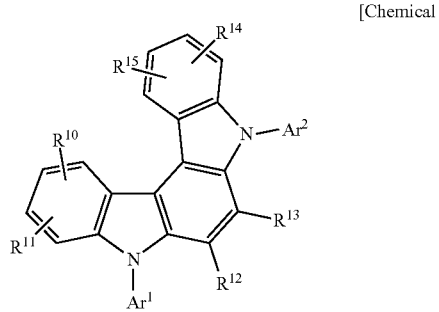

[Chemical Formula 2D]

[Chemical Formula 2E]

[Chemical Formula 2F]

[Chemical Formula 2G]

[Chemical Formula 2H]

wherein, in Chemical Formula 1A-a,
L is a single bond, or a substituted or unsubstituted phenylene group,
$R^1$ to $R^5$ are each independently hydrogen, deuterium, a substituted or unsubstituted C1 to C10 alkyl group, or a substituted or unsubstituted C6 to C18 aryl group,
$R^6$ to $R^9$ are each independently hydrogen, deuterium, a hydroxyl group, a thiol group, a substituted or unsubstituted C1 to C20 alkyl group, or a substituted or unsubstituted C6 to C18 aryl group, and
$R^6$ to $R^9$ are each independently present or adjacent groups thereof are linked with each other to form a substituted or unsubstituted dibenzofuranyl group, or a substituted or unsubstituted dibenzothiophenyl group;
wherein, in Chemical Formula 2A to Chemical Formula 2H,
$Ar^1$ is a substituted or unsubstituted phenyl group, a substituted or unsubstituted biphenyl group, or a substituted or unsubstituted naphthyl group,
$Ar^2$ is a substituted or unsubstituted biphenyl group, a substituted or unsubstituted terphenyl group, a substituted or unsubstituted naphthyl group, a substituted or unsubstituted anthracenyl group, a substituted or unsubstituted phenanthrenyl group, or a substituted or unsubstituted triphenylenyl group, and
$R^{10}$ to $R^{15}$ are each independently hydrogen, deuterium, a substituted or unsubstituted C1 to C10 alkyl group, or a substituted or unsubstituted C6 to C18 aryl group.

8. The composition for an organic optoelectronic device of claim 7, wherein at least one of $Ar^1$ and the $Ar^2$ is a substituted or unsubstituted naphthyl group.

9. An organic optoelectronic device, comprising:
an anode and a cathode facing each other, and
at least one organic layer disposed between the anode and the cathode
wherein the at least one organic layer comprises the composition for an organic optoelectronic device of claim 1.

10. The organic optoelectronic device of claim 9, wherein:
the at least one organic layer comprises a light emitting layer, and
the composition for an organic optoelectronic device is a host of the light emitting layer.

11. A display device comprising the organic optoelectronic device of claim 9.

* * * * *